(12) United States Patent
Murakami et al.

(10) Patent No.: US 7,847,147 B2
(45) Date of Patent: Dec. 7, 2010

(54) MOUSE DEVELOPING VISCERAL FAT TYPE OBESITY AND DIABETES

(75) Inventors: Noboru Murakami, Miyazaki (JP); Keiko Nakahara, Miyazaki (JP)

(73) Assignee: University of Miyazaki, Miyazaki-shi (JP)

( * ) Notice: Subject to any disclaimer, the term of this patent is extended or adjusted under 35 U.S.C. 154(b) by 462 days.

(21) Appl. No.: 11/889,593

(22) Filed: Aug. 15, 2007

(65) Prior Publication Data

US 2008/0209580 A1    Aug. 28, 2008

(30) Foreign Application Priority Data

Feb. 26, 2007 (JP) .............................. 2007-046110

(51) Int. Cl.
A01K 67/027 (2006.01)
A01K 67/00 (2006.01)

(52) U.S. Cl. .............................................. 800/9; 800/8

(58) Field of Classification Search .................... 800/9, 800/8
See application file for complete search history.

(56) References Cited

PUBLICATIONS

Allan et al. (2004) Obes. Res., vol. 12, 1397-1407.*
Lewis and Warwick et al. (1953) J. Heredity, vol. 44, 233-238.*
Sasaki et al. (2006) Japanese Society of Veterinary Science. The 142$^{nd}$ Scientific Meetin go fthe Japanese Society of Veterinary Science, Aug. 31, 2006,I-26, p. 161, English translation abstract.*
Eisen et al. (1988) J. Anim. Sci., vol. 66, 361-371.*
Japanese Society of Veterinary Science, The 142nd Scientific Meeting of the Japanese Society of Veterinary Science, Yamaguchi University, Issued Aug. 31, 2006, I-26, p. 161 (with English translation).

* cited by examiner

*Primary Examiner*—Anne Marie S Wehbe
(74) *Attorney, Agent, or Firm*—Birch, Stewart, Kolasch & Birch, LLP.

(57) ABSTRACT

An object of the present invention is to provide a mouse which has the characteristics of early developing visceral fat type obesity and also has concurrent diabetes and hyperlipemia and in which the trait is genetically established and recessively inherited. An ICR-derived mouse strain, Daruma, spontaneously developing obesity, exhibiting autosomal recessive inheritance for the trait of spontaneously developing obesity, and becoming obese only in the homozygous type is provided.

5 Claims, 26 Drawing Sheets
(5 of 26 Drawing Sheet(s) Filed in Color)

Fig. 1
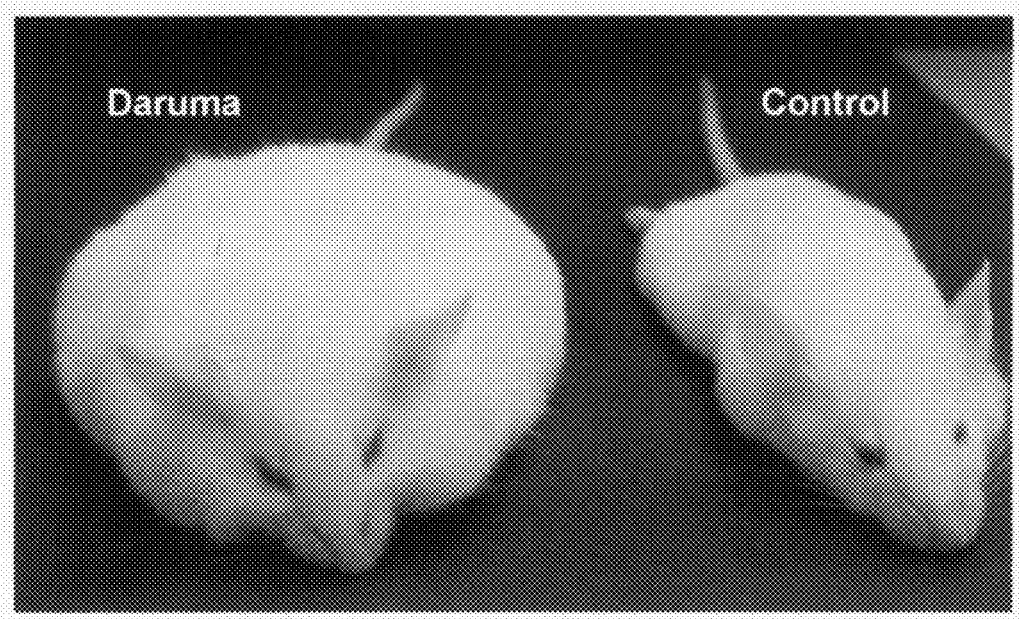
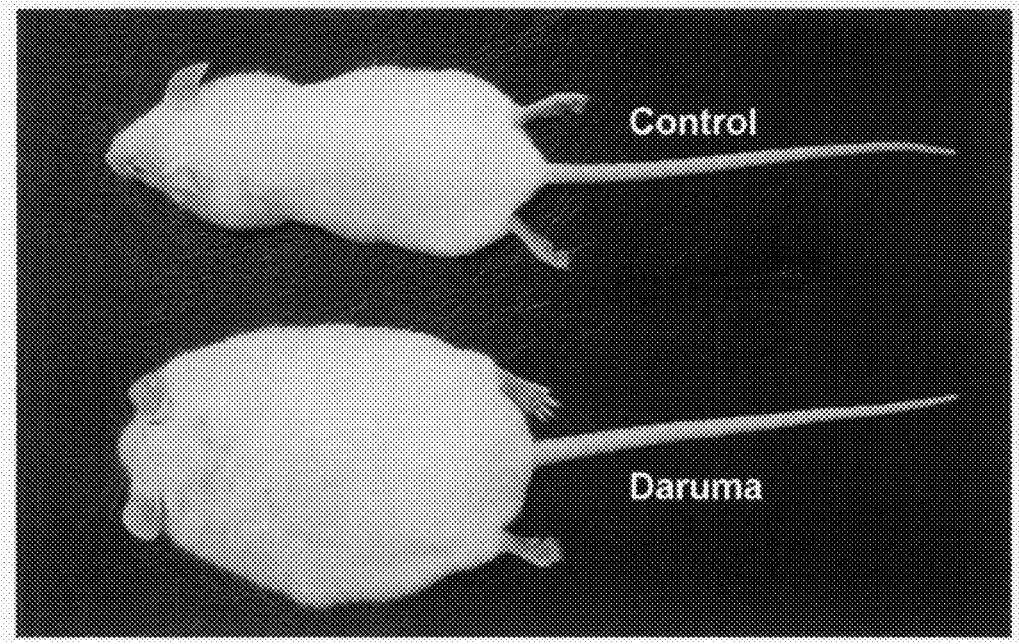

Daruma

Fig. 4-6
Behavioral Rhythm
Control
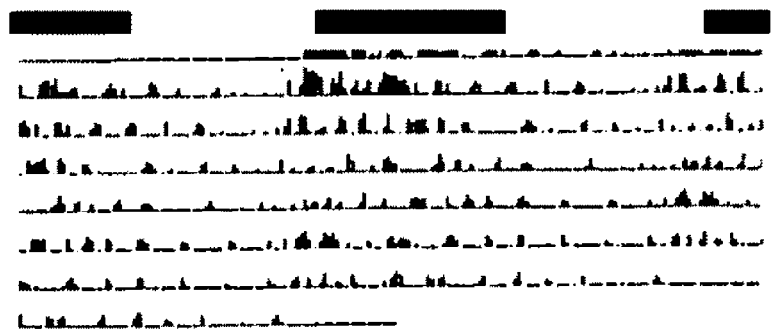
daruma
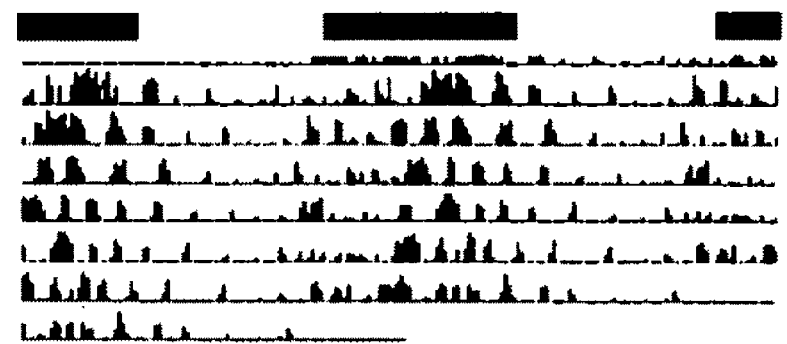

Fig. 5-1

|  | Control | daruma |
|---|---|---|
| Total Protein | 4.9 ± 0.235 | 5.35 ± 0.23274 |
| AST (GOT) | 110.3 ± 25.68 | 127.5 ± 14.9025 |
| ALT (GPT) | 32 ± 4.528 | 87.25 ± 13.8346* |
| Creatinine | 0.1 ± 0.037 | 0.06 ± 0.02041 |
| Urea Nitrogen | 18 ± 1.732 | 23 ± 1.77951 |
| Serum Glucose | 153.8 ± 9.304 | 214.5 ± 28.3975 |
| TG (Neutral Fat) | 73 ± 19.65 | 81 ± 11.0076 |
| Free Fatty Acid | 1.698 ± 0.095 | 2.4425 ± 0.15564* |
| Total Cholesterol | 116.5 ± 9.35 | 170.25 ± 12.8022* |
| HDL-Cholesterol | 72 ± 4.123 | 95 ± 1.68325* |
| LDL-Cholesterol | 8.25 ± 0.75 | 11.75 ± 2.86865 |

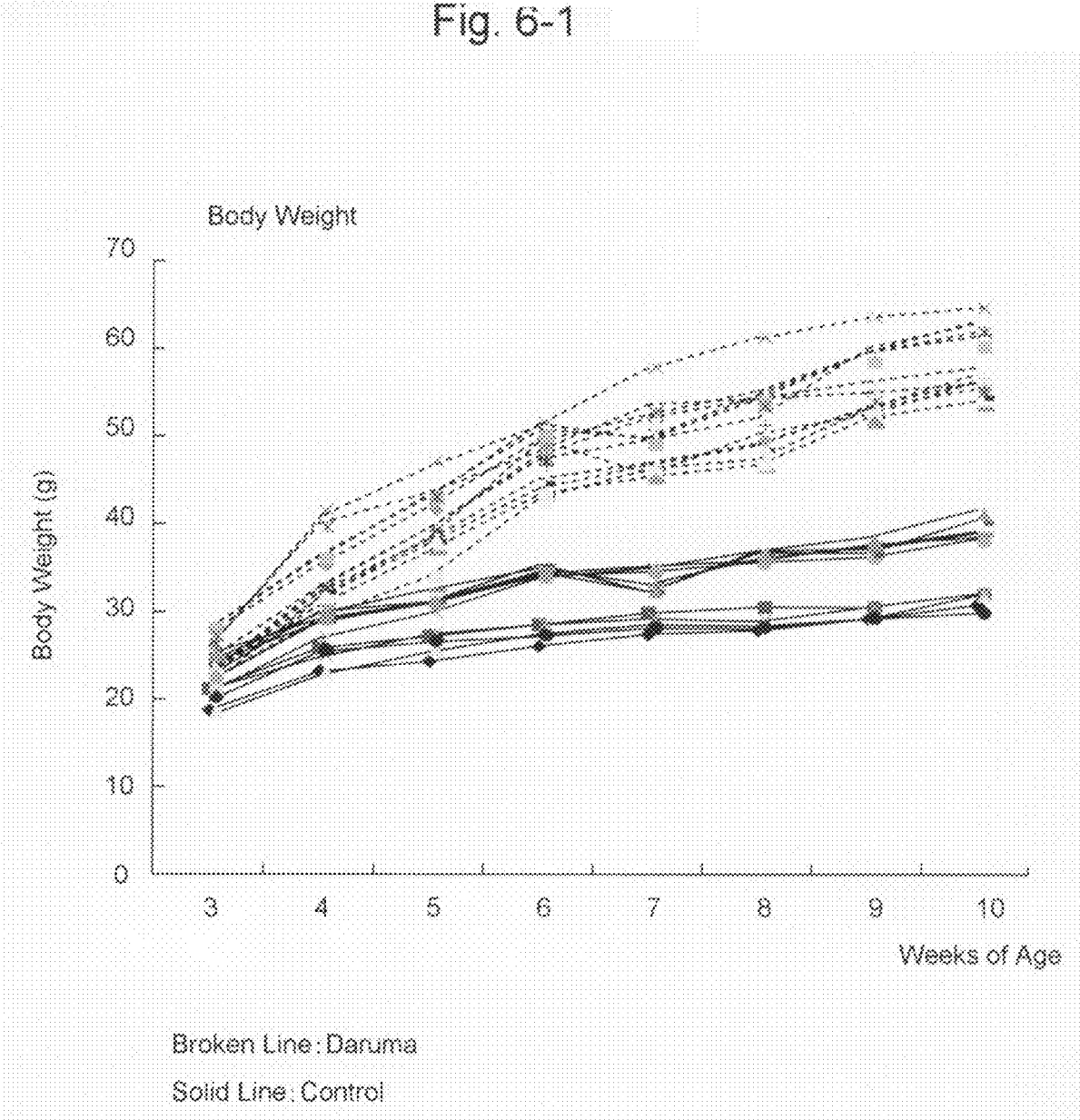

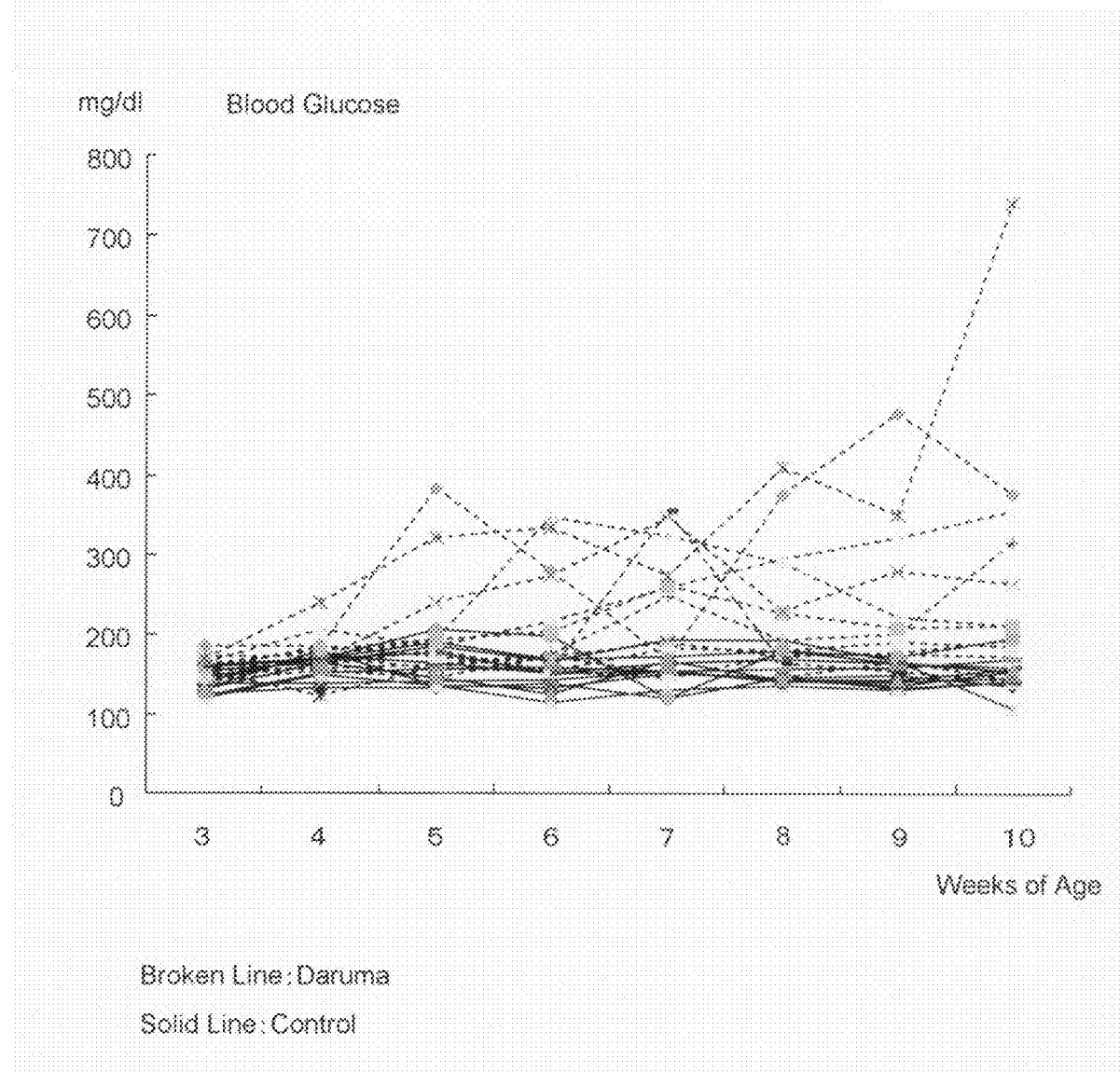

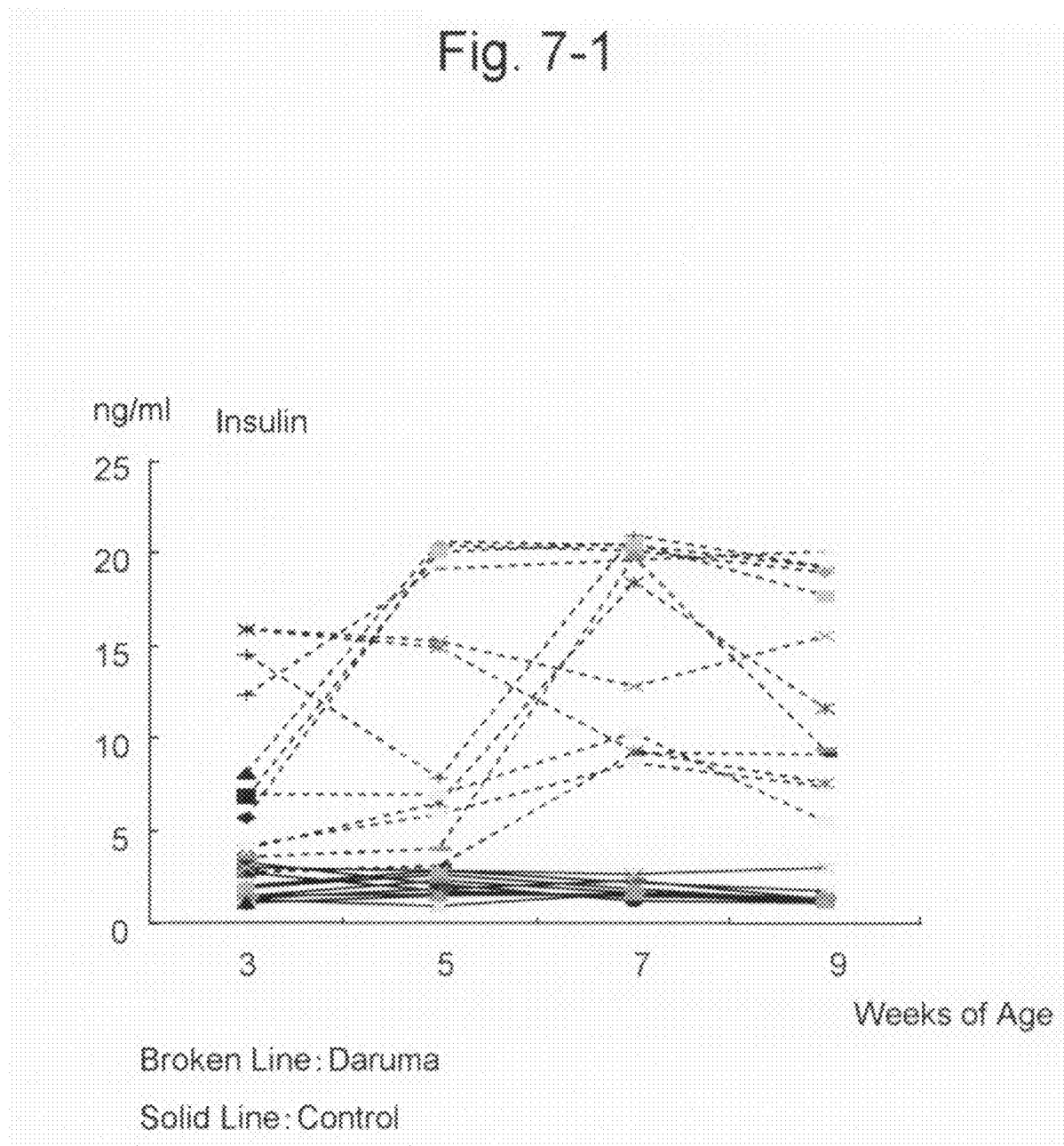

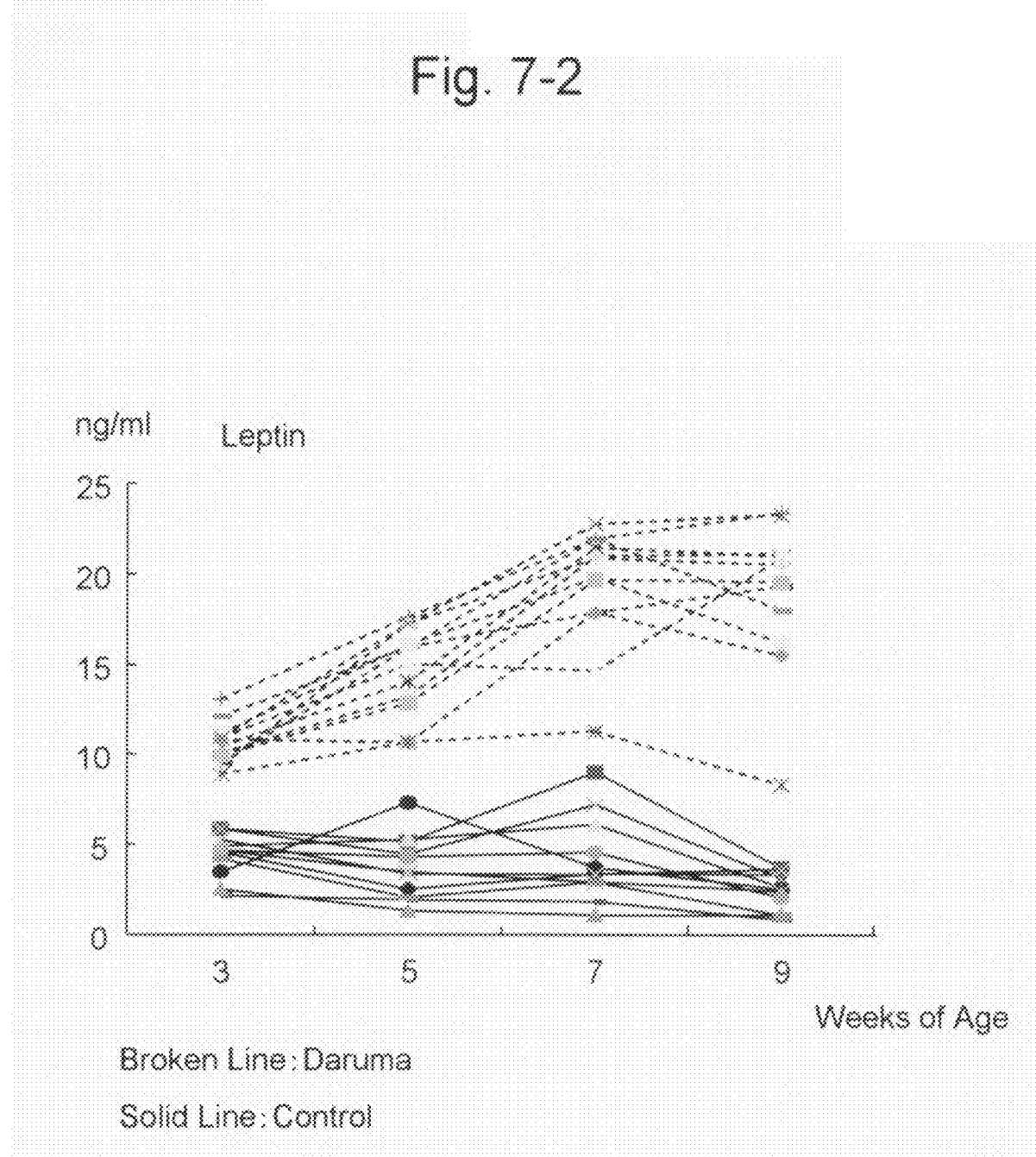

Fig. 11

Obesity Incidence Rate Based on Results of Crossing with Other Obese Model Mice

| Diabetes(db) | × | daruma : 14% |
| Obese(ob) | × | daruma : 0% |
| Fat(fat) | × | daruma : 0% |
| Tubby(tub) | × | daruma : 0% |

Theoretical Value: If the model mice have the same gene mutation as the Daruma mice, 25% of the children thereof should develop obesity.

Obesity Development in Children Born of Crossing between Daruma and db mice

A,a : Obesity-inducing Factor Unique to Daruma Mice
B,b : Obesity Induction Risk Factor
C,c : Obesity-inducing Factor Unique to db Mice Heterozygous Daruma Mice × Heterozygous db Mice

| AaBBCC | | AABBCc |
| AaBbCC | × | AABbCc |
| AabbCC | | AAbbCc |

Obesity Development

Probability of presence of all of bb, a, and c: 5/36 → 13.8%

MOUSE DEVELOPING VISCERAL FAT TYPE OBESITY AND DIABETES

BACKGROUND OF THE INVENTION

1. Field of the Invention

The present invention relates to a mouse exhibiting pathologic conditions similar to obesity and diabetes in humans.

2. Background Art

An animal model developing human disease is useful to elucidate the cause of the disease in humans or screen therapies therefor.

Obesity and diabetes have become a major problem in humans in recent years; it has been desired to elucidate pathogenic mechanisms therefor and to develop new therapeutic agents thereagainst.

Various animals have been developed as animal models for obesity and diabetes. For example, there have been reported a db/db mouse characterized by leptin receptor deletion and hyperphagia (see Diabetologia, Vol. 6: 268-273, 1970), a KK mouse (see Diabetes & metabolism, Vol. 23, Suppl 2: 38-46, 1997), an ob/ob mouse characterized by leptin gene abnormality and hyperphagia, and a mouse developing obesity and diabetes under feeding with high-fat diet (see JP Patent Publication (Kokai) No. 2005-110632).

However, these mice took long to develop obesity or diabetes, and did not show a significant degree of obesity in a short period of time. In addition, the mouse described in patent document 1 was not a mouse in which the trait of spontaneously developing obesity was genetically established.

To elucidate the pathogenic mechanism of human obesity and diabetes and develop a therapeutic agent therefor, there has been required a model animal spontaneously developing obesity and diabetes like humans and having characteristics of human obesity and diabetes. The present invention meets such demands and is intended to provide a mouse which has the characteristics of early developing visceral fat type obesity and also having concurrent diabetes and hyperlipemia and in which the trait is genetically established and recessively inherited.

SUMMARY OF THE INVENTION

The present inventors screened 32,000 mice for spontaneous obese mice to develop a new model animal of human obesity and diabetes and have established genetically obese mice by repeating the crossing thereof. The obese mice exhibit an autosomal recessive inheritance and become obese only in the homozygote. The mice also develop diabetes concomitantly with obesity. The mice have typical visceral fat type obesity and have been found to be useful for researches of metabolic syndromes or the like. The present inventors have designated the newly established strain of mice as Daruma.

Specifically, the present invention is as follows.

(1) A mouse strain, Daruma, derived from ICR mice, spontaneously developing visceral fat type obesity, exhibiting autosomal recessive inheritance for the trait of spontaneously developing the visceral fat type obesity, and becoming obese only in the homozygote.

(2) The mouse strain Daruma described in item (1), further having at least one of the characteristics of:
   (i) having concurrent diabetes; and
   (ii) having concurrent hyperlipemia.

(3) The mouse strain Daruma described in item (1) or (2), wherein the visceral fat type obesity is developed at four weeks of age.

(4) The mouse strain Daruma described in any one of items (1) to (3), wherein the strain is obtained from a fertilized ovum having an accession number of FERM ABP-10888.

(5) A method for producing, from ICR mice, a mouse strain, Daruma, spontaneously developing visceral fat type obesity, exhibiting autosomal recessive inheritance for the trait of spontaneously developing the visceral fat type obesity, and becoming obese only in the homozygote, comprising the steps of:

(a) selecting mice with obesity from ICR mice to back cross the selected mice with the ICR mice;

(b) selecting mice with obesity from FT mice obtained at step (a) to cross the F1 mice with obesity with each other;

(c) selecting mice with obesity from child mice obtained at step (b) to cross the mice with obesity with each other; and (d) selecting offspring mice spontaneously developing obesity.

(6) The method for producing a mouse strain, Daruma, described in item (5), wherein step (c) is repeated.

(7) The method for producing a mouse strain, Daruma, described in item (6), wherein the strain further has at least one of the characteristics of:
   (i) having concurrent diabetes; and
   (ii) having concurrent hyperlipemia.

(8) A mouse strain, Daruma, obtained by the method described in any one of items (5) to (7).

(9) A human obesity and/or diabetes model mouse, wherein the mouse is a mouse of the strain Daruma described in any one of items (1) to (4) and (8).

(10) A method for evaluating, or screening for, health foods for preventing obesity or agents for treating obesity or diabetes, comprising administrating a test substance to mice of the strain Daruma described in any one of items (1) to (4) and (8).

The obese mouse strain Daruma of the present invention early develops intense visceral fat type obesity compared to conventional model mice of obesity and diabetes. The obesity of the obese mouse strain Daruma of the present invention is autosomally recessively inherited; thus, the strain develops the obesity only in the heterozygote. This enables the number of the mice to be made up as needed. The obesity mouse strain Daruma of the present invention can be used not only as a model for basic research of obesity, feeding, energy metabolism or diabetes but also as a model for drug discovery or evaluation of health foods.

BRIEF DESCRIPTION OF THE DRAWINGS

The patent or application file contains at least one drawing executed in color. Copies of this patent or patent application publication will be provided by the office upon request and payment of the necessary fee.

FIG. 1 is a set of photographs showing a comparison of appearance between obese Daruma mice and conventional mice;

FIG. 2-1 is a graph showing growth curves of obese Daruma and conventional female mice;

FIG. 2-2 is a graph showing growth curves of obese Daruma and conventional male mice;

FIG. 3-1 is a diagram showing CT scan images of a conventional mouse;

FIG. 3-2 is a diagram showing CT scan images of an obese Daruma mouse;

FIG. 4-1 is a graph showing a comparison of physiological function between obese Daruma mice and conventional mice: comparison of food intake;

FIG. 4-2 is a graph showing a comparison of physiological function between obese Daruma mice and conventional mice: comparison of behavioral amount;

FIG. 4-3 is a graph showing a comparison of physiological function between obese Daruma mice and conventional mice: comparison of blood pressure;

FIG. 4-4 is a graph showing a comparison of physiological function between obese Daruma mice and conventional mice: comparison of body temperature;

FIG. 4-5 is a graph showing a comparison of physiological function between obese Daruma mice and conventional mice: comparison of heart rate;

FIG. 4-6 is a chart showing a comparison of physiological function between obese Daruma mice and conventional mice: comparison of behavioral rhythm;

FIG. 5-1 is a diagram showing the results of biochemical examination of blood between obese Daruma mice and conventional mice;

FIG. 5-2 is a graph showing a comparison of AST level between obese Daruma mice and conventional mice;

FIG. 5-3 is a graph showing a comparison of ALT level between obese Daruma mice and conventional mice;

FIG. 5-4 is a graph showing a comparison of TG level between obese Daruma mice and conventional mice;

FIG. 5-5 is a graph showing a comparison of total cholesterol level between obese Daruma mice and conventional mice;

FIG. 5-6 is a graph showing a comparison of HDL-cholesterol level between obese Daruma mice and conventional mice;

FIG. 6-1 is a graph showing a comparison of body weight between obese Daruma mice and conventional mice;

FIG. 6-2 is a graph showing a comparison of blood glucose level between obese Daruma mice and conventional mice;

FIG. 7-1 is a graph showing a comparison of insulin level between obese Daruma mice and conventional mice;

FIG. 7-2 is a graph showing a comparison of leptin level between obese Daruma mice and conventional mice;

FIG. 8-1 is a graph showing a comparison of blood glucose level in a glucose tolerance test between obese Daruma mice and conventional mice;

FIG. 8-2 is a graph showing a comparison of insulin level in a glucose tolerance test between obese Daruma mice and conventional mice;

FIG. 11 is a diagram showing the results of experiment of crossing with other obese model mice.

DETAILED DESCRIPTION OF THE PREFERRED EMBODIMENTS

Figures 1, 2:
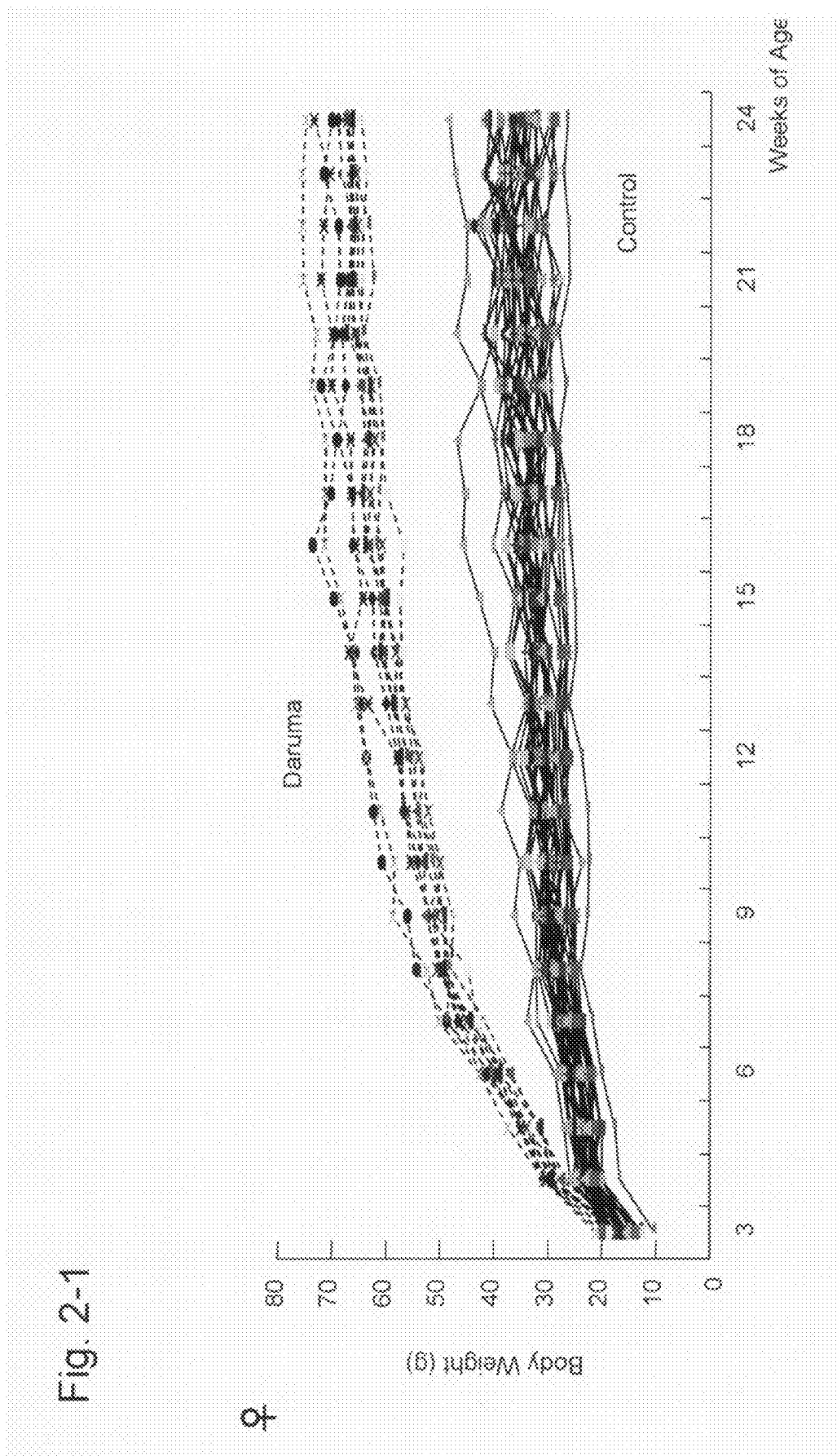
Figure 2:
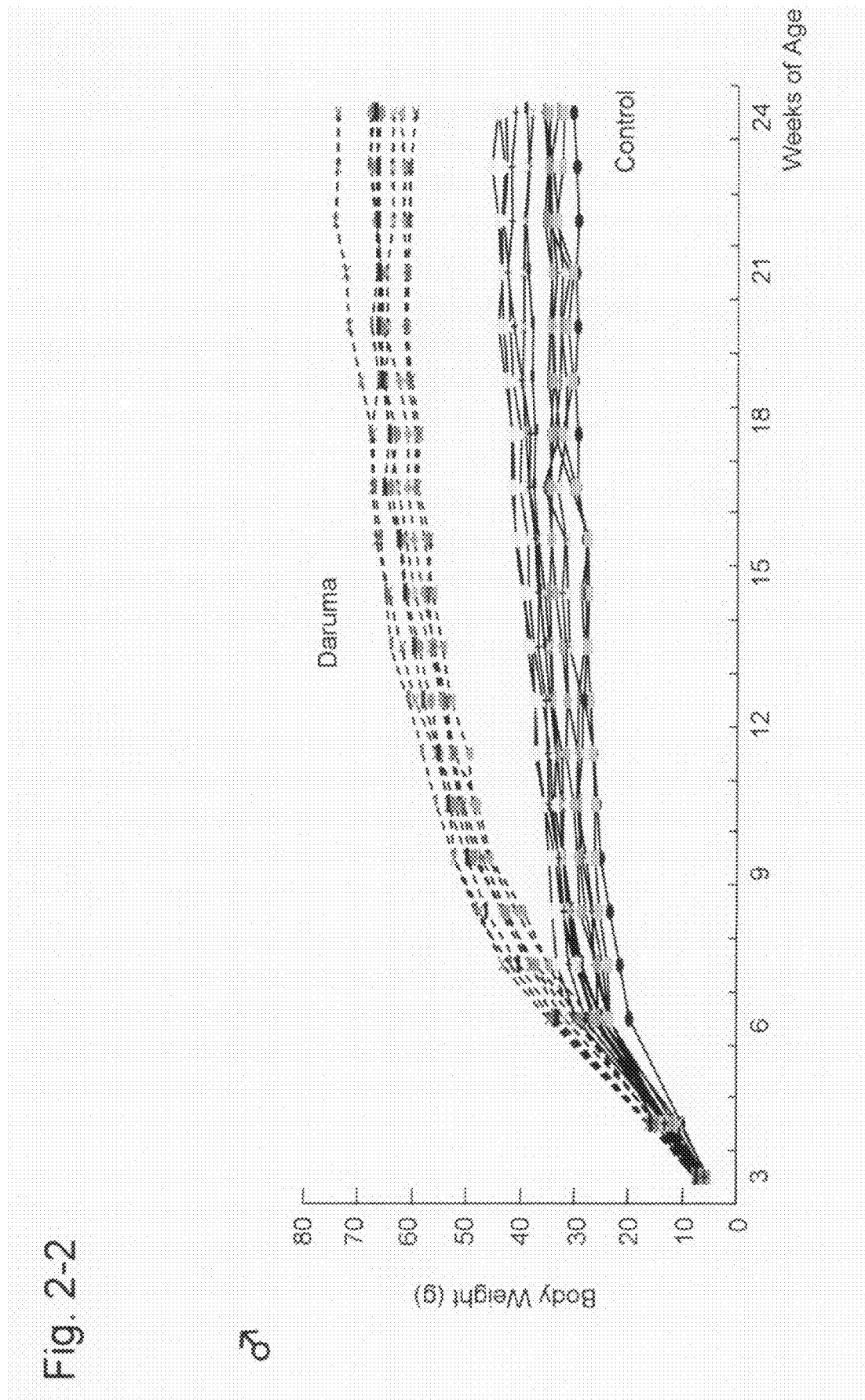

The present invention is described below in detail.

The mouse strain of the present invention can be established by the following method.

Spontaneous obese mice are selected from ICR mice. Here, as the spontaneous obese mice, there are selected individuals having the feature of having an average body weight of 136.3 weight % for males or 130.7 weigh % for females based on that of conventional mice at four weeks of age and of about two times thereof for both males and females at ten weeks of age. The selected spontaneous obese mice are back crossed with the ICR mice to provide F1 mice. The F1 mice do not spontaneously develop obesity because they have a gene associated with the spontaneous obesity in heterozygote. Subsequently, the F1 mice are crossed with each other to provide F2 mice. Twenty-five percent of the F2 mice spontaneously develop obesity. In addition, the F2 mice are crossed with each other to provide mice 100% spontaneously developing obesity. At this stage, the mouse strain spontaneously developing obesity according to the present invention can be established. The crossing of the F2 mice with each other may be further repeated.

The mouse strain thus obtained is homozygous for the trait of spontaneously developing obesity; the trait is autosomally recessively inherited.

The finally established strain of mice in which the trait of obesity is stably retained and inherited is referred to as "Daruma".

The mouse strain Daruma of the present invention is genetically stable; the crossing between mice of the strain Daruma can provide Daruma mice as offsprings.

The fertilized ovum of the obese mouse strain Daruma of the present invention has been deposited Feb. 21, 2007 under Accession Number FERM ABP-10888 (labeled as "Daruma mouse fertilized ovum" for identification) in International Patent Organism Depositary, National Institute of Advanced Industrial Science and Technology (located at Tsukuba Central 6, 1-1-1 Higashi, Tsukuba, Ibaraki, Japan).

The mouse strain Daruma can be obtained from Murakami Laboratory, Department of Agriculture, National University Corporation Miyazaki University.

The obesity mouse strain Daruma of the present invention has the following features.

(1) The mice have a high degree of obesity; the adult mice have body weights of about two times or more those of conventional mice. In this respect, "conventional mice" refers to normal mice which are not developing obesity and diabetes and have normal blood fat levels.

(2) The obesity is visceral fat type barrel obesity.

(3) The mice develop obesity at the early stage of 4 weeks of age. In addition, the obesity progresses rapidly. Both of the males and females of the mice develop obesity.

(4) The mice have a markedly increased visceral fat mass compared to conventional mice. In the abdominal white dead tissue of mice of the obese strain Daruma, adipocytes are swollen with fat and the size of the cells is increased. In addition, droplets of fat accumulate in the liver, which results in fatty liver.

(5) The mice develop concomitant diabetes. Specifically, the mice have an elevated blood insulin level compared to conventional mice. The elevation is observed from 3 weeks of age. In the adult mice, the blood insulin level is preferably elevated to 1.5 times or more, more preferably 2 times or more that in conventional mice. The blood glucose level is also significantly increased compared to that in conventional mice. In addition, in a glucose tolerance test, 1 to 3 hours after glucose loading, the blood insulin level is preferably elevated to 1.5 times or more, more preferably 2 times or more that in conventional mice and the blood glucose level is preferably increased to 1.5 times or more, more preferably 2 times or more that therein.

The incidence rate of the diabetes is 100% for males and less than 10% for females, showing that the incidence rate is different between the males and females.

The blood leptin level is also elevated. The elevation is observed from 3 weeks of age. In the adult mice, the blood leptin level is preferably elevated to 1.5 times or more, more preferably 2 times or more that in conventional mice.

The elevations in the blood glucose, insulin and leptin values are observed at an early stage, for example, at 4 weeks of age.

(6) The mice develop hyperlipemia. Here, "hyperlipemia" refers to a state in which the level of lipid present in the blood is high compared to that of conventional mice. The obesity mouse strain Daruma of the present invention has the feature of being high in total cholesterol, HDL-cholesterol and free fatty acid compared to conventional mice. The total cholesterol level is 20% or more, preferably 30% or more higher than that of conventional mice. The HDL-cholesterol level is 15% or more, preferably 20% or more higher than that of conventional mice. The free fatty acid level is 20% or more, preferably 30% or more higher than that of conventional mice. In addition, fat accumulates in the liver to increase the ALT (alanine aminotransferase) (GPT) level. The ALT level is 50% or more, preferably 100% or more, more preferably 200% or more higher than that of conventional mice.

However, the obesity mouse strain Daruma of the present invention has a blood TG level not different from that of conventional mice.

(7) The obesity mouse strain Daruma of the present invention has a slightly increased food intake during the night compared to conventional mice, but no significant difference is observed in the food intake per day therebetween.

(8) The mice show a reduction in the amount of behavior per day compared to conventional mice.

The obesity mouse strain Daruma of the present invention develops obesity and diabetes bearing a striking resemblance to human obesity and diabetes and can be used as a model animal for human obesity and diabetes.

The obesity mouse strain Daruma of the present invention also has symptoms bearing a close resemblance to human metabolic syndromes and can be used as a model animal for human metabolic syndromes.

The obesity mouse strain Daruma of the present invention shows differences described below from other obesity model mice.

The obesity of the strain Daruma has been found to be complicated by type-2 diabetes; as type-2 diabetes model mice having obesity, there have previously been known ob/ob, db/db, lethal Yellow, fat and tubby mice exhibiting these symptoms due to single-gene abnormality and NSY, KKAy, NZO, TSOD and TallyHo mice showing the symptoms due to multi-factorial gene abnormality.

It has been reported that the ob/ob mice start to develop obesity from about 4 to 5 weeks of age like the strain Daruma, show hyperphagia due to the loss of a leptin signal from adipocytes, and exhibit diabetes-like hyperglycaemia, reduced glucose tolerance, hyperinsulinaemia, decreased fecundity, hypometabolism, hypothermia and the like. The ob/ob mice do not develop the hyperinsulinaemia until the body weight thereof excessively increases; thus, the mice are thought to develop the hyperinsulinaemia as a result of the obesity. In this respect, the ob/ob mice greatly differ from the strain Daruma.

The db/db mice start to develop obesity from about 4 to 5 weeks of age like the strain Daruma and show hyperphagia, polydipsia, and polyuria; the blood glucose level thereof abruptly increases at 4 to 8 weeks of age unlike that of the strain Daruma and rises with increasing body weight. It has been reported that the plasma insulin level shows a high value at the early stage of 10 to 14 days after birth and that the urine sugar positive rate reaches nearly 100% irrespective of sex just beyond 10 weeks of age. This is different from the case of the strain Daruma having the high incidence rate of diabetes for males.

The lethal Yellow mice are one of 5 variants due to a dominant single-gene mutation in agouti gene locus, have slowly-progressing obesity unlike Daruma, ob/ob and db/db mice, and feature insulin resistance, hyperleptinemia, leptin resistance, infertility, and the like.

The fat mice start to develop obesity at the late stage of 6 to 8 weeks of age unlike the strain Daruma and also show hyperglycaemia, hyperleptinemia, and hyperinsulinaemia. In the ob/ob and db/db mice, the insulin level is decreased when diabetes occurs and becomes severe with the progression. In contrast, the fat mice have been reported to chronically have a high insulin level. The time course of insulin level is also a difference from the strain Daruma because Daruma has shown an change in the insulin level. In addition, it is known that the fat mice show these symptoms only for males and do not have diabetes-like symptoms for females.

The tubby mice start to develop obesity at the late stage of 9 to 12 weeks of age unlike the strain Daruma; the progression thereof is similar to that in the Yellow obese mice. The blood glucose level is normal or low, and the insulin level gradually increases with each passing week and reaches that corresponding to hyperinsulinemia. The tubby mice have also been reported to show hyperleptinemia.

When hematological findings are compared among the above strains of mice, the TG (triglyceride) level has been 1.5 to 2 times the normal level in the ob/ob, db/db, lethal Yellow and tubby mice, while showing normal value in the fat and Daruma mice. The plasma cholesterol level has been noted to increase in the ob/ob, db/db, lethal Yellow, fat and tubby mice, which is due mainly to an elevation in the HDL-cholesterol level. Some differences have been observed in the degree of hypercholesterolemia among the strains: the plasma cholesterol level has shown a high elevation in the ob/ob and db/db mice and a slight increase in the fat, male lethal Yellow and male tubby mice. In contrast, the strain Daruma has shown chronically increased values of high cholesterol and HDL-cholesterol levels.

The NSY mice are derived from ICR mice like the strain Daruma. They do not show serious obesity or hyperinsulinemia, but feature insulin resistance, reduced insulin responsiveness to glucose, hyperglycaemia, and the like. It has been reported that the NSY mice develop diabetes from 8 weeks of age on and that the development occurs in about 10% of the males and on the order of 20% of the females by 48 weeks of age.

The KKAy mice are prepared by introducing an Ay gene generated by dominant single-gene mutation in agouti gene locus into KK mice showing mild obesity and glucose intolerance. It has been reported that they show marked obesity and glucose intolerance and hyperinsulinaemia and feature insulin resistance.

It has been reported that the NZO mice feature hyperphagia, obesity and insulin resistance, and, with the progression thereof, show damaged pancreatic islet cells, hypoinsulinemia and marked hyperglycaemia. The males thereof start to show hyperglycaemia between 12 and 22 weeks of age, while the females show no progression of hyperglycaemia or hypoinsulinemia until 22 weeks of age. The hyperglycaemia in the males is correlated with the insulin level: the insulin level is observed to decrease with increasing blood glucose. The NZO mice also show high levels of TG and plasma cholesterol.

It has been reported that the TSOD mice are a strain established from a ddY strain by selective crossing using the body weight gain and urinary glucose level as indexes, and feature hyperphagia, increased water intake, obesity, hyperglycaemia, hyperinsulinemia, and enlarged pancreatic islets.

The TallyHo mice already have obesity, hyperinsulinemia, and hyperleptinemia at 4 weeks of age. In this respect, they are similar to the strain Daruma; however, these symptoms of the TallyHo mice are different from those of the strain Daruma in that the symptoms occur without associated hyperglycaemia. The TallyHo mice have also been reported to feature a marked elevation in the TG level.

The mouse strain of the present invention can be used as the following model animal and animal for evaluation.

1. A model for analyzing the cause of excessive accumulation of visceral fat
2. A model animal for analyzing diabetes
3. A model animal for analyzing genetic obesity
4. A model animal for analyzing genetic diabetes
5. A model animal for studying lipid metabolism
6. A model animal for analyzing the mechanism of feeding
7. A model animal for comparison with an existing obesity-related substance
8. A model animal for analyzing the relationship between obesity and exercise
9. An animal for evaluation in the development of health foods for preventing obesity
10. An animal for evaluating therapeutic agents for obesity
11. An animal for evaluating therapeutic agents for diabetes Those skilled in the art can use the obesity mouse strain Daruma in combination with a known method for the analyses described in items 1 to 8 above.

Among the above, the animals for evaluation in the development of health foods and for evaluating therapeutic agents for obesity and diabetes can be used to evaluate therapeutic or preventive effects of known health foods and compounds against obesity and diabetes and further to screen for new health foods effective in preventing obesity and compounds usable for treating or preventing obesity and diabetes. As used herein, the term "health foods" includes not only a health food but also a food for specified health use, a food with nutrient function claims, a nutritional supplementary food, and a supplement. Here, the food for specified health use refers to a food labeled to the effect that it can be ingested for specified health care in dietary life to expect the purpose of the health care to be achieved.

In order to evaluate, or screen for, a health food effective in preventing obesity or a therapeutic agent for obesity or diabetes, a known health food, a therapeutic agent for obesity or diabetes, or a test substance whose effect is to be determined may be administered to the obesity mouse strain Daruma of the present invention to perform the evaluation or screening on the basis of whether a change is observed in the characteristics of the obesity mouse strain of the present invention described in items (1) to (8) above. For example, a test substance can be evaluated or determined as effective if the substance is administered to provide the suppression of the body weight gain, the inhibition of visceral fat accumulation, the mitigation of diabetes, and/or the alleviation of hyperlipemia.

EXAMPLES

The present invention will be specifically described based on the following Examples. However, the invention is not intended to be limited by these Examples.

Example 1

Establishment of the Obesity Mouse Strain Daruma

Two mice having obesity were discovered in 2005 among ICR mice maintained in the Laboratory of Veterinary Physiology, Department of Veterinary Medicine, Faculty of Agriculture, Miyazaki University. Suspecting the possibility that the obesity had been caused by gene mutation, we performed the following experiment. The mice having obesity were subjected to back crossing. As a result, some of their children developed obesity. Accordingly, speculating that a problem was present on gene, we purchased wild ICR mice from Charles River Laboratories Japan, Inc. to cross with the obese mice. Consequently, no F1 mice developed obesity; however, obesity occurred at an incidence rate of about 25% when the F1 mice were crossed with each other. Subsequently, when these obese mice were crossed with each other, the resultant mice were all obese. In addition, a cross was repeated between the wild and obese mice, between the heterozygous mice, and between the obese homozygous mice to prepare a pedigree chart. As a result, a value of 0% was obtained for the cross between the wild mice and between the homozygous and wild mice; 48% (theoretical value: 50%), between the heterozygous and homozygous mice; 25% (theoretical value: 25%), between the heterozygous mice; and 100% (theoretical value: 100%), between the homozygous mice. From these results, it was speculated that the obesity is caused by recessive inheritance. Accordingly, the obese mice (homozygous) were crossed with mice of a different strain (BALB/c) (wild) to examine whether the obesity gene was conserved or not. None of the born F1 mice (theoretically heterozygous) developed obesity, but the cross between the F1 mice produced some mice developing obesity. Then, heterozygous mice were selected from the F1 mice and again crossed with the wild BALB/c mice to provide F2 mice. Heterozygous mice were again selected from the F2 mice (when the cross between an F2 mouse and a homozygous obese ICR mouse produced an obese mouse, the F2 mouse is interpreted as a heterozygous mouse) and further again crossed with the BALB/c mice (wild). This was repeated to produce two generations of congenic mice. In this period, the obesity gene was retained. The obese mice were also found to show a high leptin level at weaning age (3 weeks) without reaching maturity. Thus, it turned out that this could be used as an index for screening for homozygous mice. The above results have demonstrated that the obese mice exhibit an autosomal recessive inheritance.

Example 2

Comparison of Physiological and Biochemical Characteristics Between Obese Daruma Mice and Conventional Mice (1) Comparison of Appearance FIG. 1 shows a comparison of appearance between obese Daruma mice and conventional mice. The obese mice and conventional mice were each born from the same parent. As depicted in the figure, the obese Daruma mice featured visceral fat type barrel obesity.

(2) Comparison of Growth Curves

The body weight of obese Daruma mice and conventional mice was measured from 3 to 24 weeks of age. Ten each of males and females were used for both of the obese Daruma and conventional mice. FIG. 2 shows growth curves thereof. FIG. 2-1 shows growth curves of the females, and FIG. 2-2 shows those of the males. A body weight difference occurred between the females of both strains of mice from 4 weeks of age and between the males thereof from 6 weeks of age; twice as much body weight difference occurred from 15 weeks of age on. These differences were all ascribed to visceral fat.

(3) Comparison of CT Scan Images

Figures 1, 3:
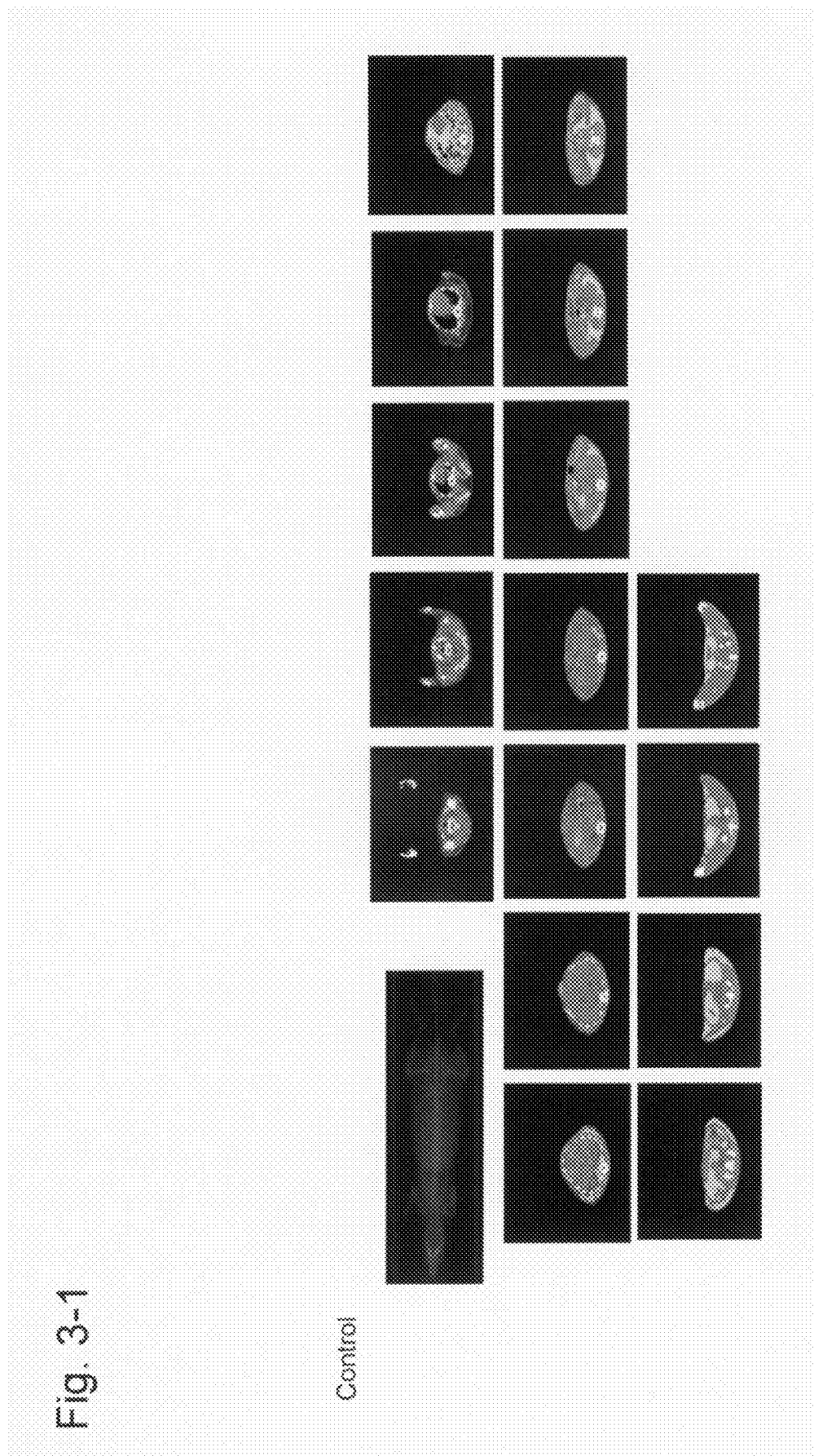
Figures 2, 3:
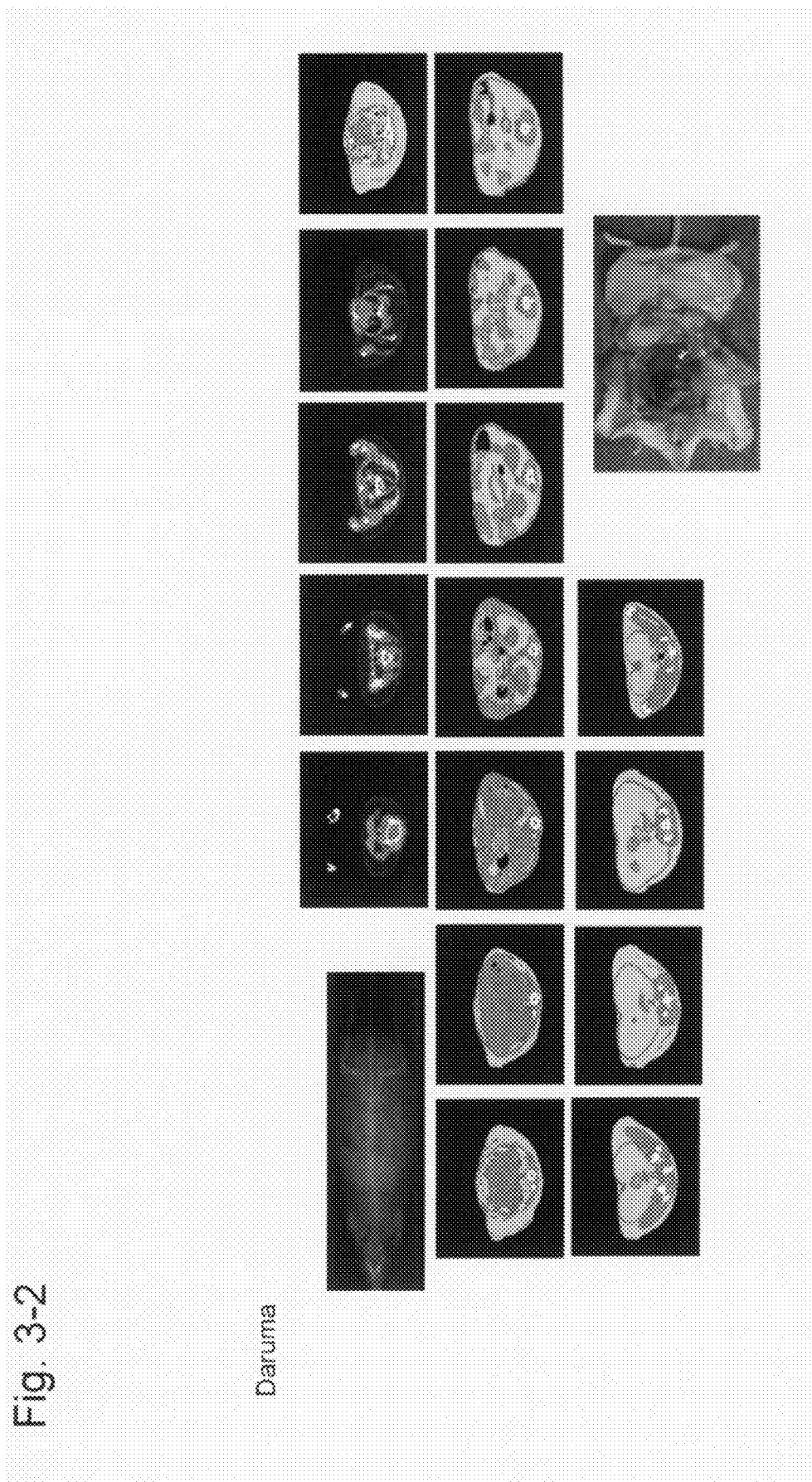

The CT scan images of 13-week old obese Daruma and conventional mice were taken using the X-ray CT apparatus LaTheta (from ALOKA Co., Ltd.) for experimental animals. FIG. 3 shows the CT scan images of both mice. FIG. 3-1 is the CT scan image of the conventional mouse, and FIG. 3-2 is that of the obese Daruma mouse. In the figures, the light blue portions represent fat. The obese Daruma mouse showed a marked increase in the visceral fat mass compared to the conventional mouse. When the obese Daruma mouse was subjected to ventrotomy, an abundant accumulation of fat was observed particularly in the abdomen, similar to the results obtained by the CT scan.

(4) Comparison of Physiological Functions

Four- to nineteen-week old obese Daruma and conventional mice were measured for food intake, behavioral amount, blood pressure, body temperature, heart rate, and behavioral rhythm. For the food intake, there were measured food intake during the light period (L: rest period) and the dark period (D: activity period) and total daily food intake. For this purpose, 5-, 6-, 7- and 9-week old mice (wild and obese) were bred in L for 12 hours and in D for 12 hours and accommodated to powdered feed for one week. The food intake was measured immediately after 7 o'clock lighting and just before 19 o'clock lights-out. The behavioral amount was measured using a behavioral tracing analyzer from Muromachi Kikai Co., Ltd., for measuring the movement of an animal by an infrared sensor.

FIGS. 4-1, 4-2, 4-3, 4-4, 4-5 and 4-6 show the food intake, behavioral amount, blood pressure, body temperature, heart rate, and behavioral rhythm, respectively.

The food intake slightly increased during the night in the obese Daruma mice, but did not show any great difference between the light and dark periods. The behavioral amount showed a significant decrease during the light and dark periods and the whole day (L+D) in the obese Daruma mice. The blood pressure showed a significant increase in the obese Daruma mice of up to 7 weeks of age. The body temperature showed no significant difference between the obese Daruma and conventional mice. The heart rate significantly increased in the obese Daruma mice.

The behavioral rhythm showed no abnormality (any abnormality in the rhythm will affect various physiological functions such as food intake, behavioral amount and metabolism; however, the obesity cannot be said to be caused by rhythm disturbance because the rhythm was normal).

(5) Comparison of Biochemical Examinations of Blood

Figures 1, 4:
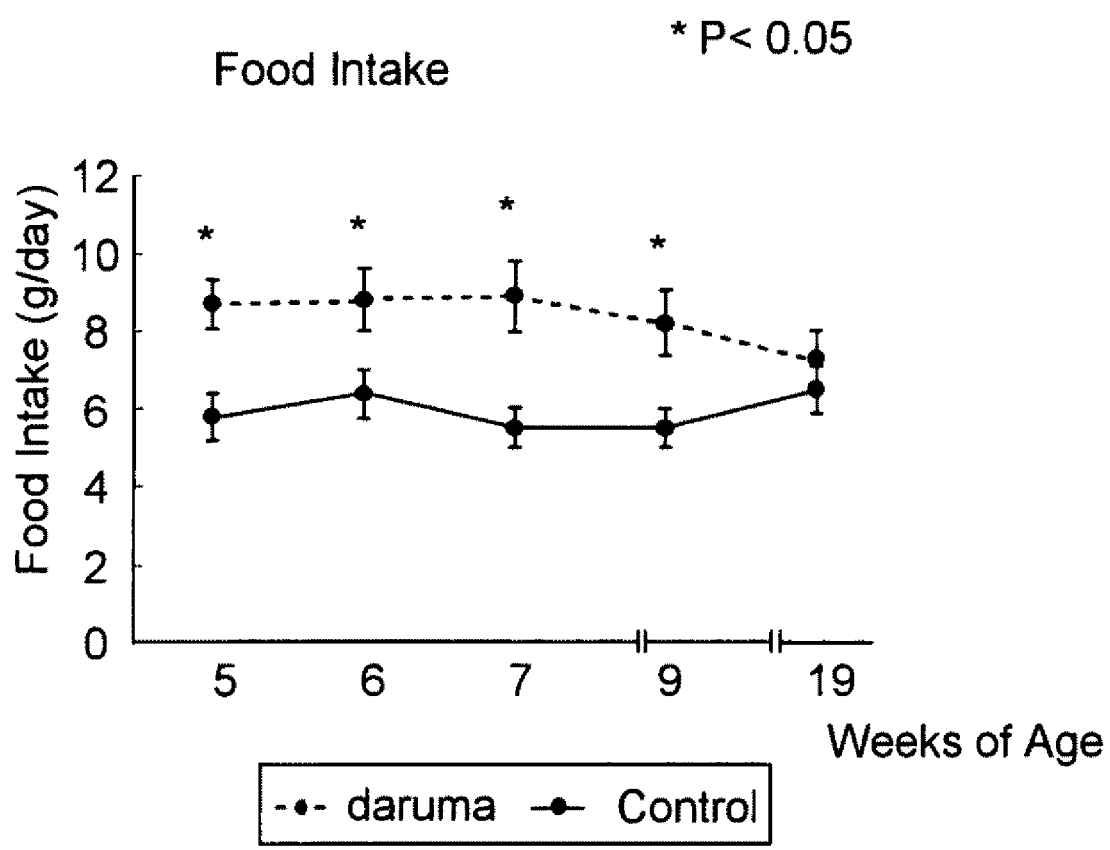
Figures 2, 4:
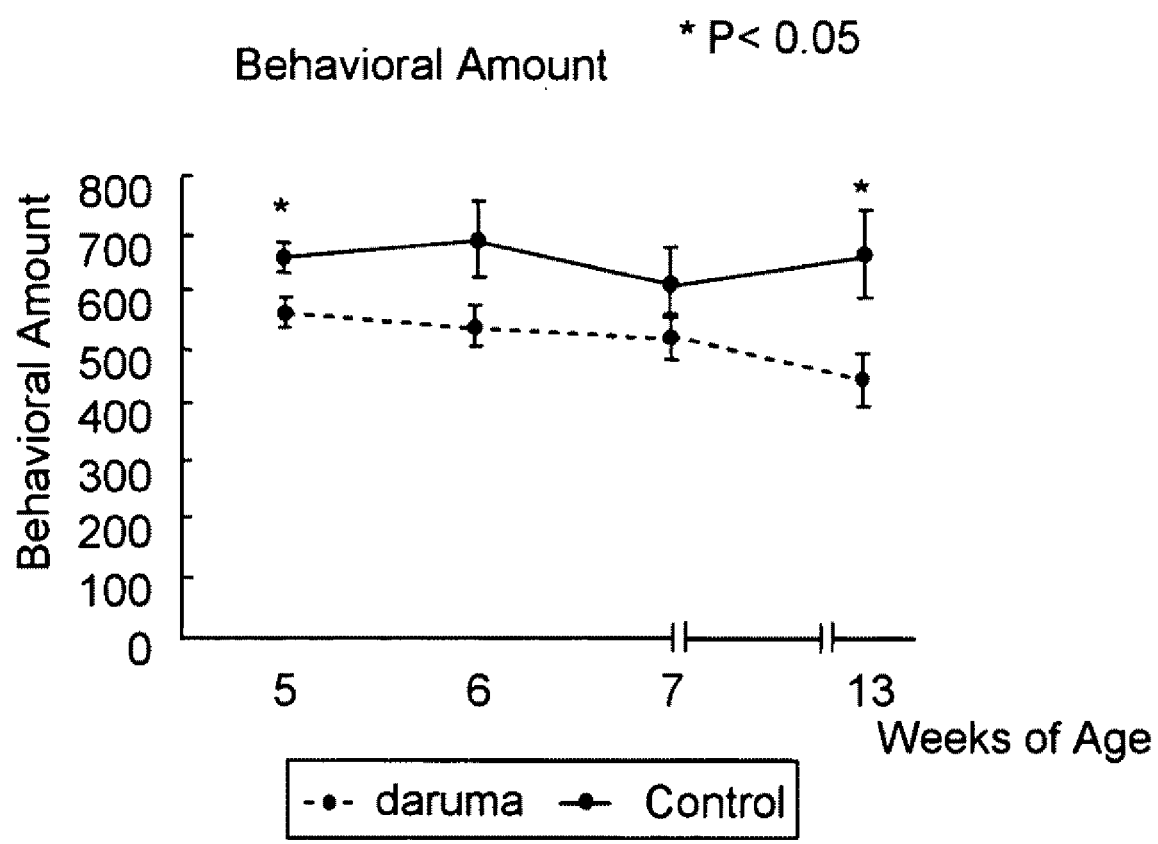
Figures 3, 4:
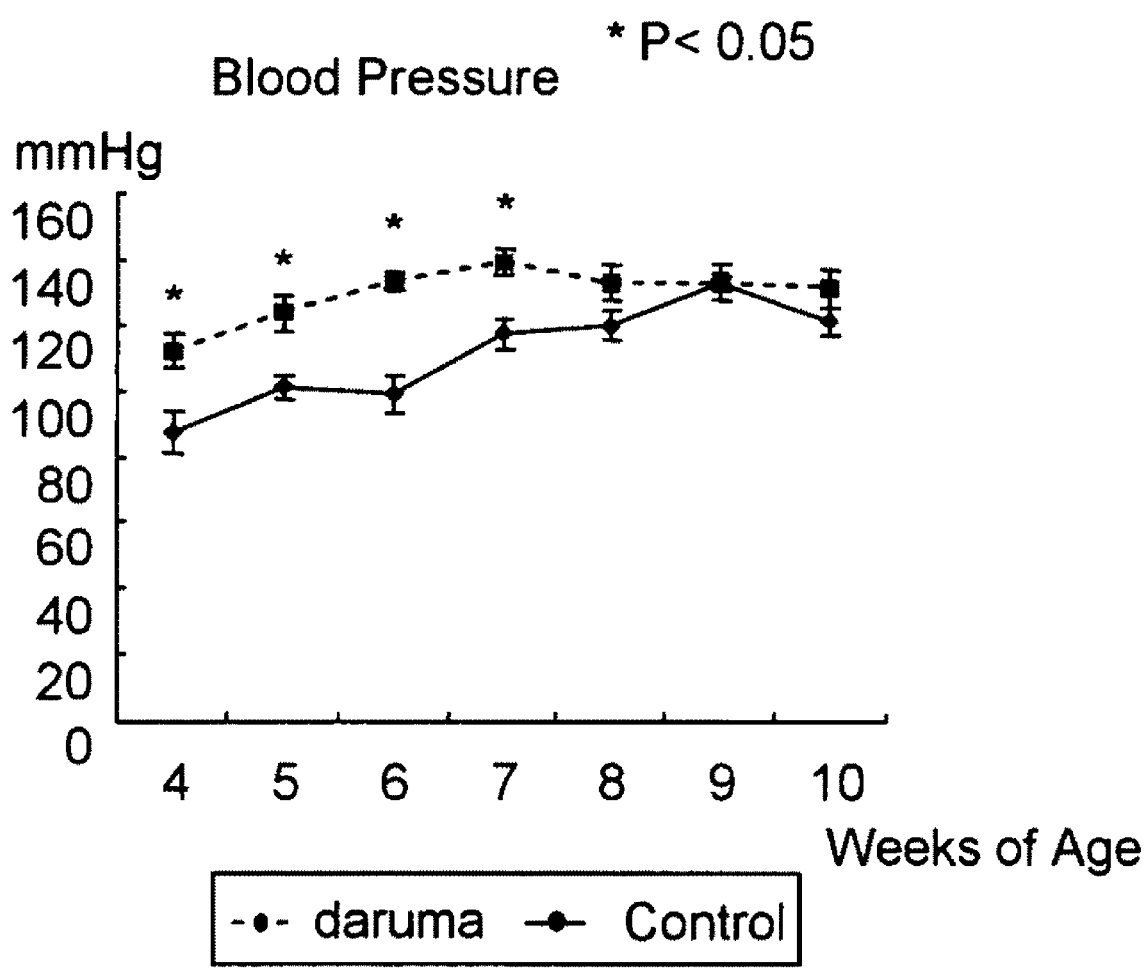
Figure 4:
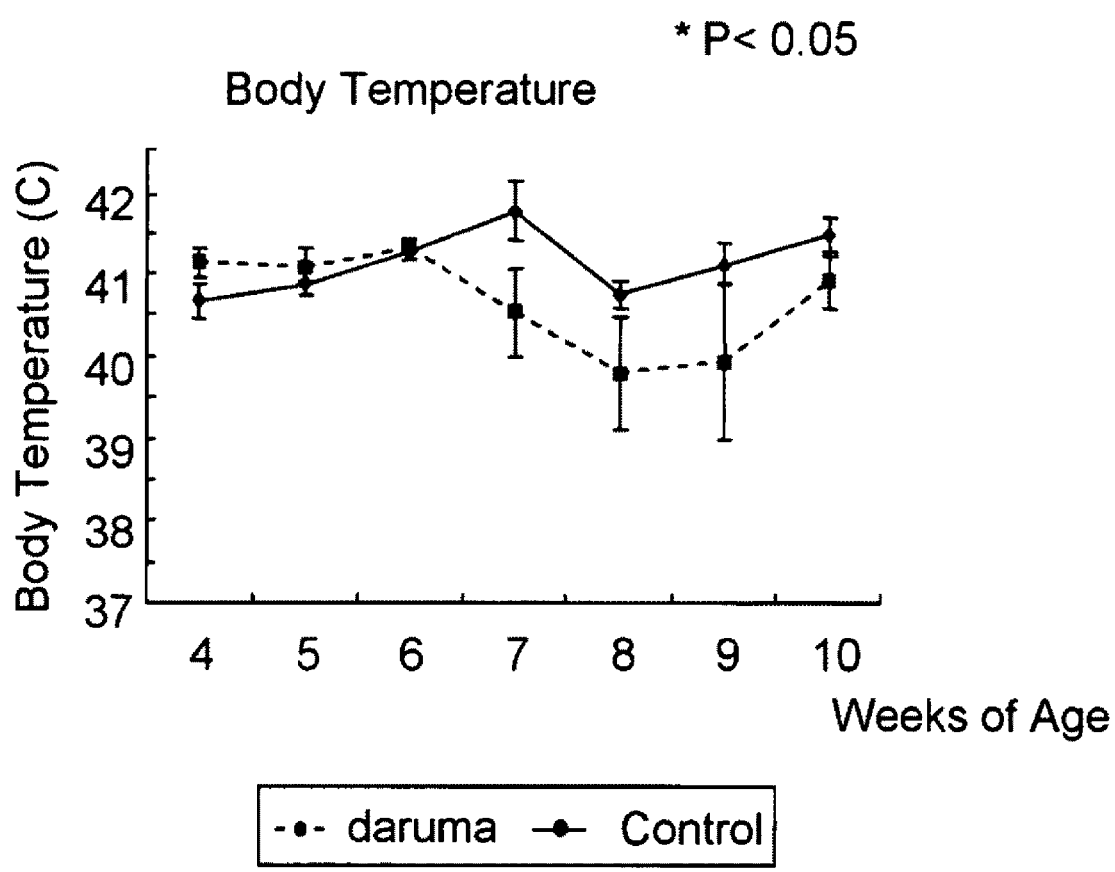
Figures 4, 5:
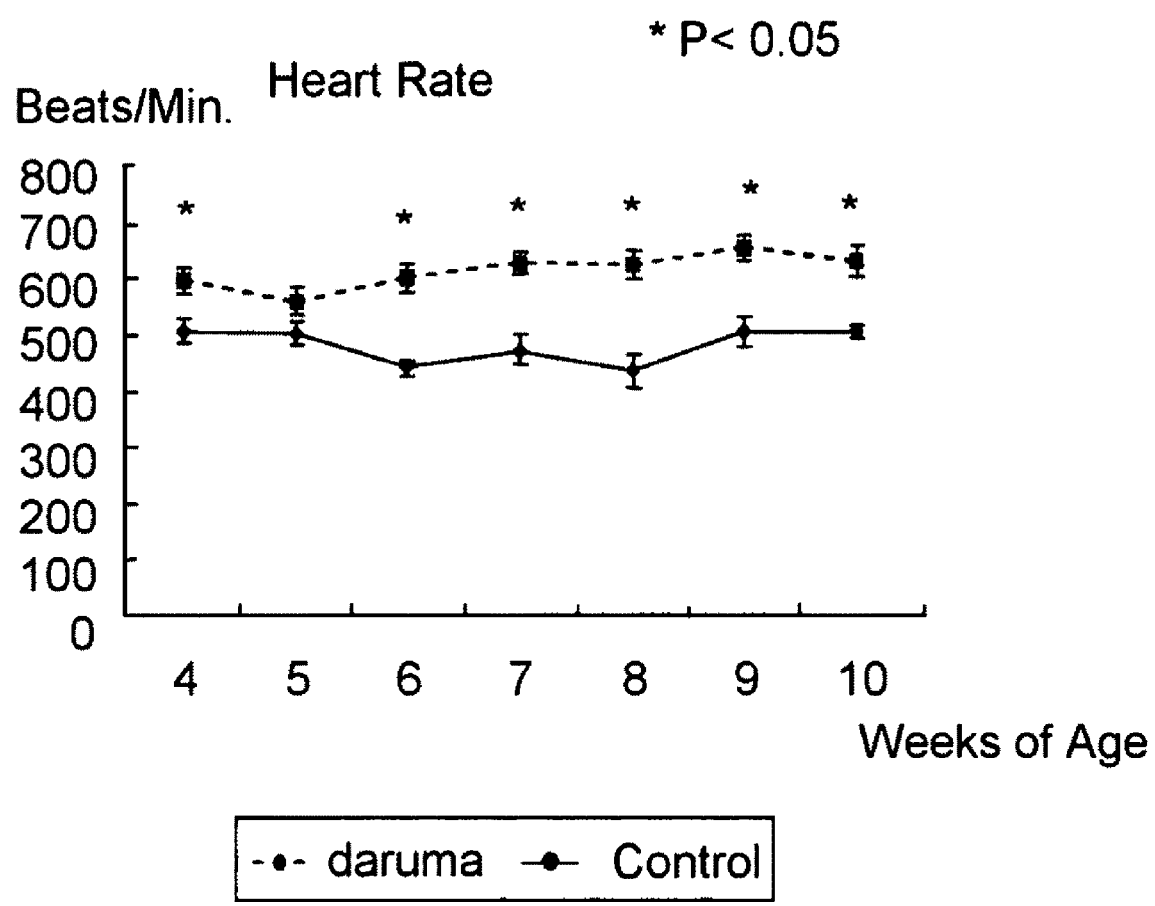

Blood was collected from 4-, 5-, 9- and 10- to 13-week old obese Daruma and conventional mice to perform the biochemical examination thereof. Each value was measured by use of DRI-CHEM 3500V (from FUJIFILM). The items examined were total protein, AST, ALT, creatinine, urea nitrogen, serum glucose, TG, free fatty acid, total cholesterol, HDL-cholesterol, and LDL-cholesterol. FIG. 5-1 shows the mean results in the 10- to 13-week old mice (adult mice). FIGS. 5-2, 5-3, 5-4, 5-5 and 5-6 show AST, ALT, TG, total cholesterol and HDL-cholesterol levels, respectively, in 4-, 5- and 9-week old mice. The obese Daruma mice had significantly high levels of ALT, free fatty acid, total cholesterol and HDL-cholesterol compared to the conventional mice. On the other hand, no significant differences were observed in the levels of total protein, AST, creatinine, urea nitrogen, serum glucose, TG, and LDL-cholesterol between the obese Daruma and conventional mice.

(6) Comparison of the Blood Glucose, Insulin and Leptin Levels

Blood was collected from obese Daruma and conventional mice of up to 10 weeks of age to measure glucose, insulin and leptin in the blood. The body weight of each mice was also measured simultaneously. The blood glucose was measured using DRI-CHEM 3500V (from FUJIFILM). Using 10 µl of plasma as a sample, the insulin was measured with Levis Insulin Kit Mouse-T (from Shibayagi Co., Ltd.). The reaction was conducted according to the operating manual attached to the kit and after the end of all steps, the absorbance was measured (at a dominant wavelength of 450 nm and a secondary wavelength of 620 nm). In addition, a standard curve was prepared to determine the measurement results. Using 5 µl of plasma as a sample, the leptin was measured with Morinaga Leptin Kit (from Morinaga Institute of Biological Science, Inc.). The reaction was conducted according to the operating manual attached to the kit, and after the end of all steps, the absorbance was measured (at a dominant wavelength of 450 nm and a secondary wavelength of 630 nm). Further, a standard curve was prepared to determine the measurement results.

Figures 2, 5:
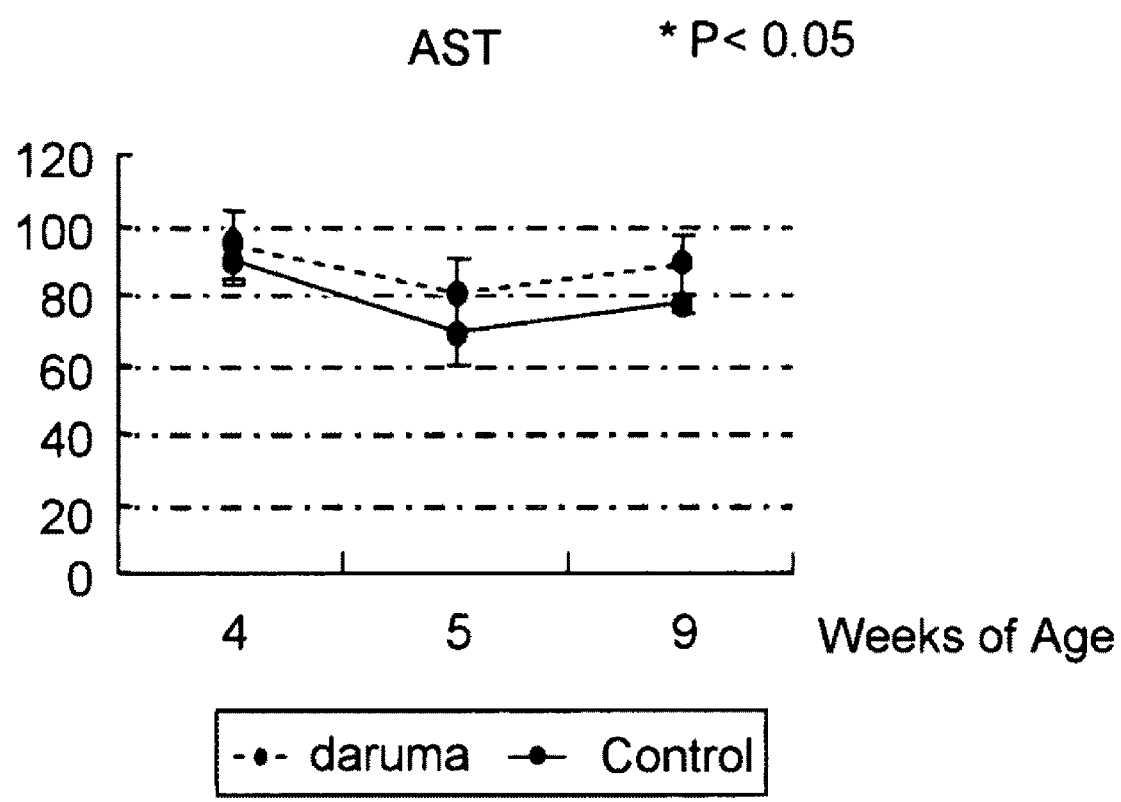
Figures 3, 5:
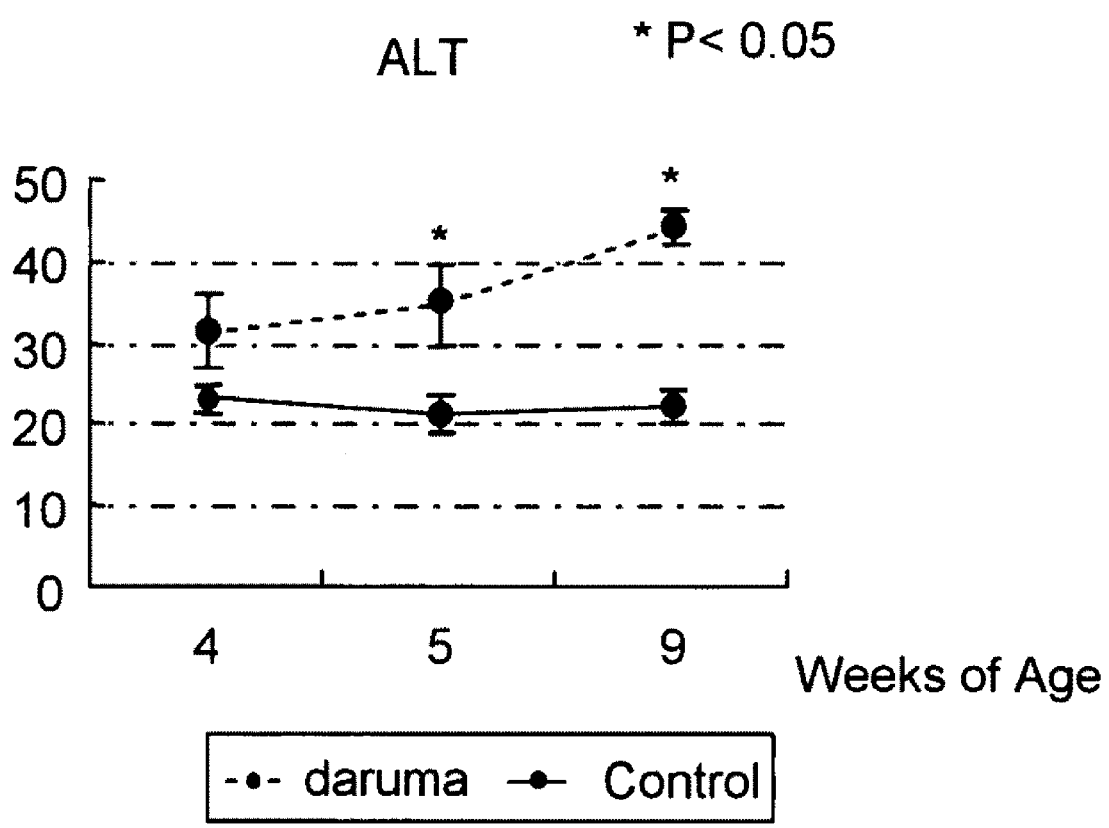
Figures 4, 5:
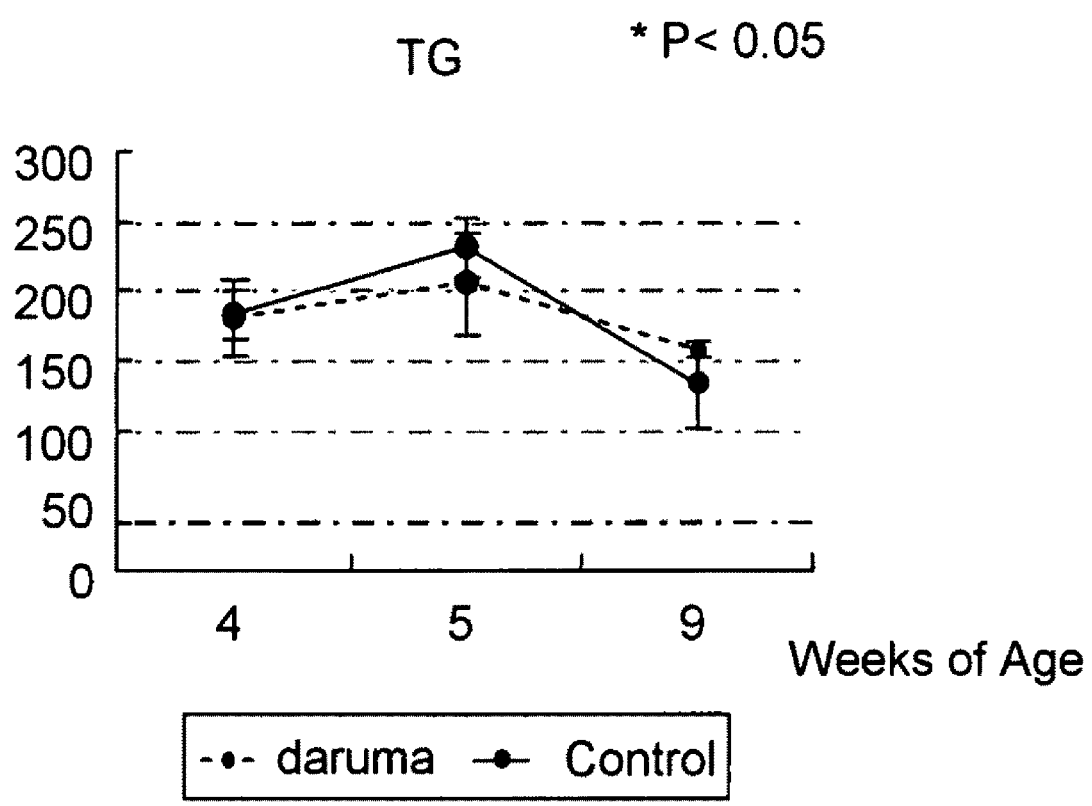
Figure 5:
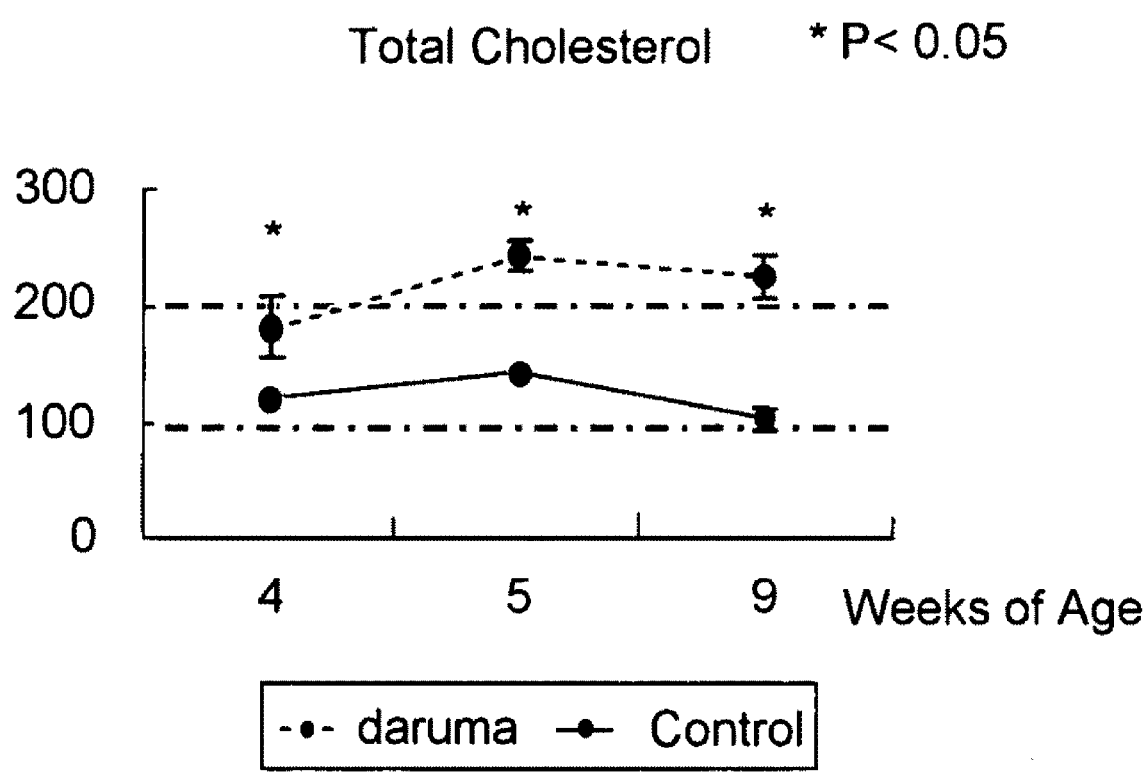
Figures 5, 6:
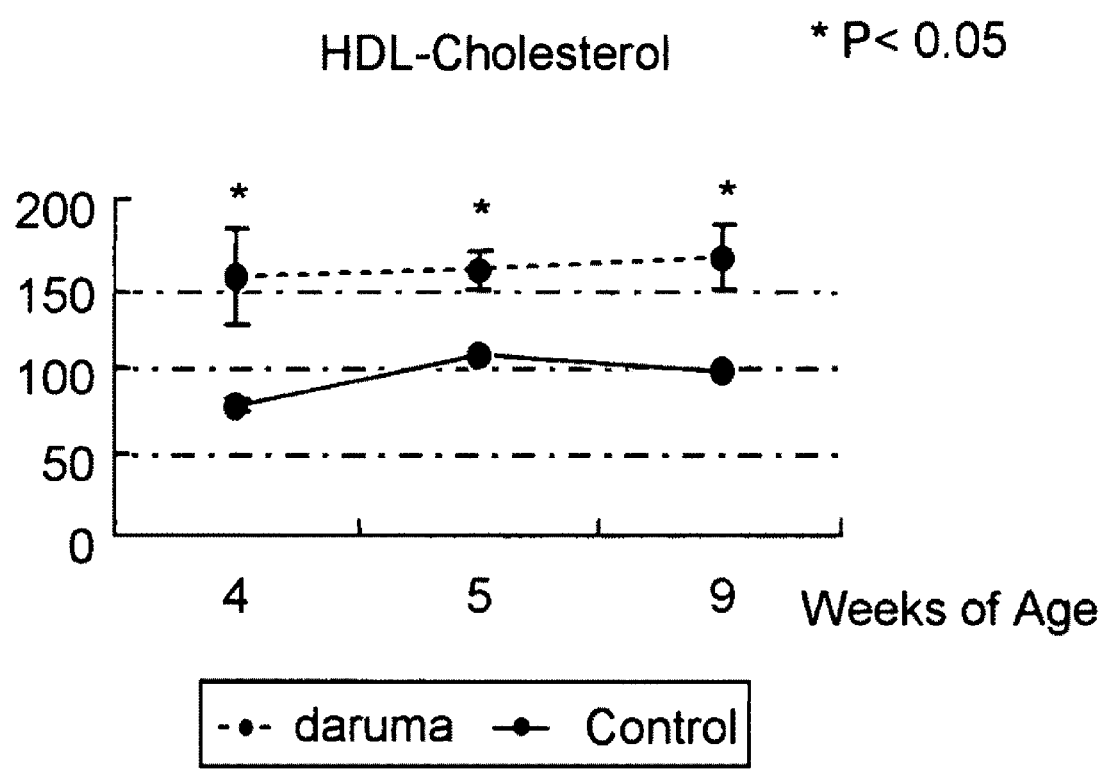

FIG. 6-1 shows the body weights, and FIG. 6-2 depicts the blood glucose levels. FIG. 7-1 shows the insulin levels, and FIG. 7-2 depicts the leptin levels. The blood glucose level was high in the Daruma mice compared to that in the normal mice. The level unexceptionally fell within the range of 100 to 200 mg/dl in all of the normal mice, while being 200 mg/dl or more in most of the Daruma mice. The incidence rate of diabetes was 100% in males of the Daruma mice, while being less than 10% in females thereof. Blood glucose level varies depending on various factors such as individual difference, blood sampling time, and stress; thus, it is difficult to find a definite tendency for the variation even when the blood is collected from the same individual every week. Nevertheless, there was probably no doubt that the Daruma mice developed hyperglycemia because these mice obviously had a higher level of blood glucose from about 4 to 5 weeks of age. The obese Daruma mice also had higher levels of blood insulin and leptin from 3 weeks of age.

In addition, a glucose tolerance test was performed. Specifically, glucose was intraperitoneally administered at a dose of 1.5 g/kg body weight; blood was collected by the above blood collection method just before administration and 30, 60, 120 and 180 minutes after administration to measure the blood glucose and insulin levels. The animals used were 8 to 12 each of normal and Daruma male mice of 4- to 8-weeks of age.

Figures 1, 8:
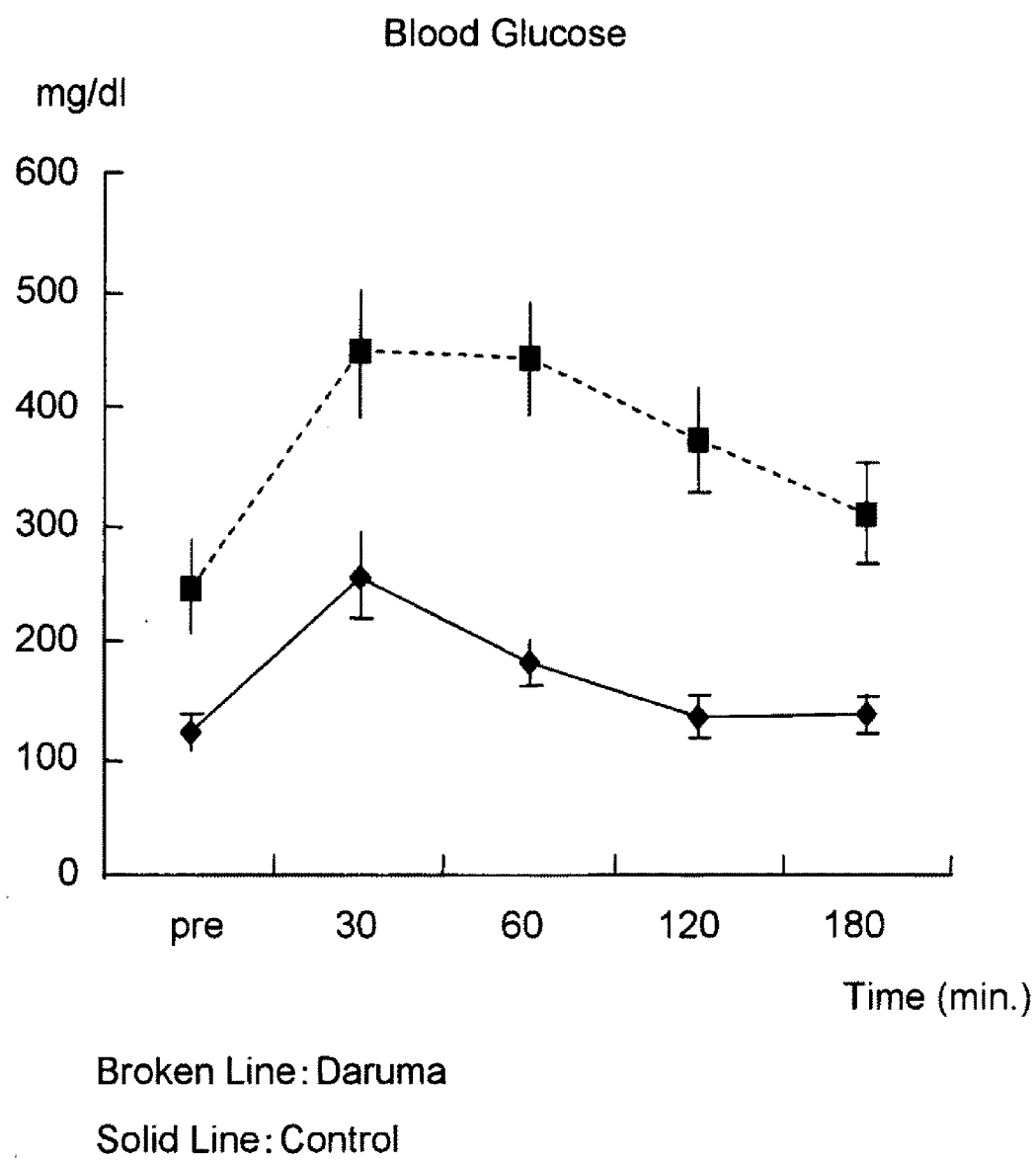
Figures 2, 8:
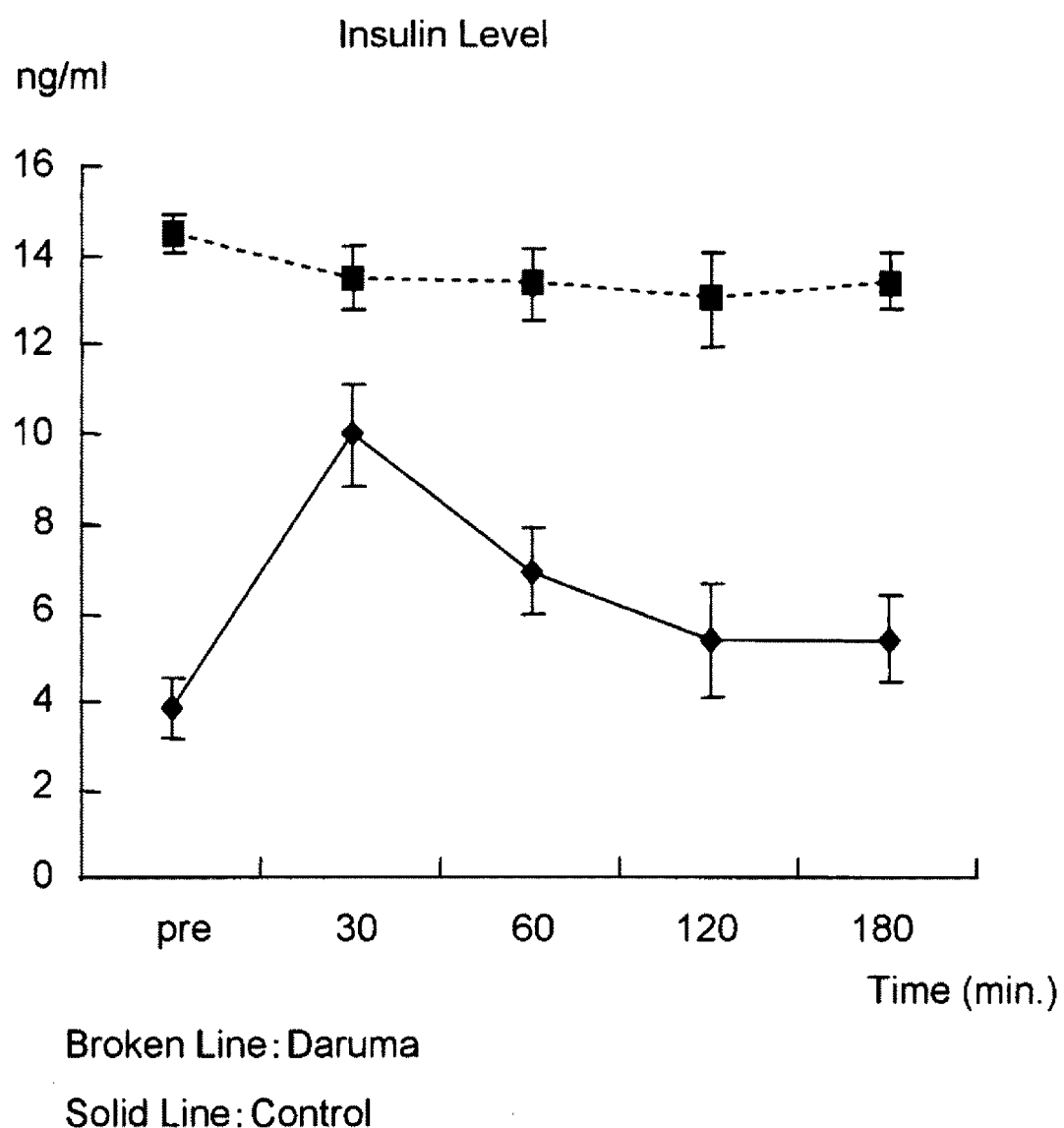

FIG. 8-1 shows the blood glucose levels, and FIG. 8-2 depicts the insulin levels. In the glucose tolerance test, the blood glucose and insulin levels are significantly higher in the obese Daruma mice than in the conventional mice.

(7) Comparison of the Fat and Liver

Figure 9:
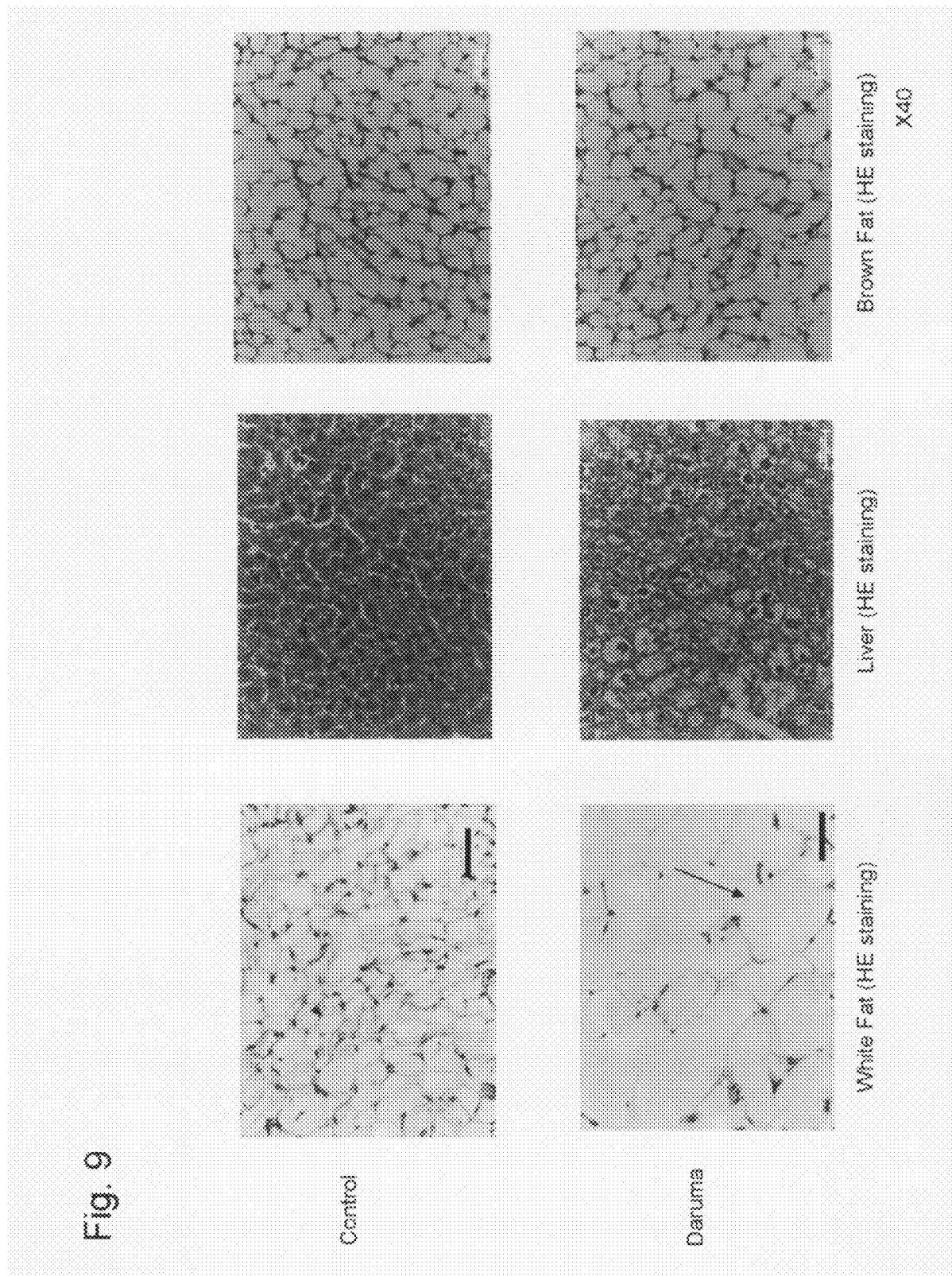
FIG. 9 is a set of photographs showing HE staining images of abdominal fat and liver tissue sections between an obese Daruma mouse and a conventional mouse.

Abdominal fat (white fat and brown fat) and liver were removed from obese Daruma and conventional mice to prepare tissue sections thereof, which were then subjected to HE staining for microscopic observation. FIG. 9 shows HE staining images thereof. In the obese Daruma mouse, white adipocytes were swollen with fat and enlarged; fat droplets accumulated in the liver.

(8) Comparison of the Pancreas, Kidney and Muscle Tissue

Figure 10:
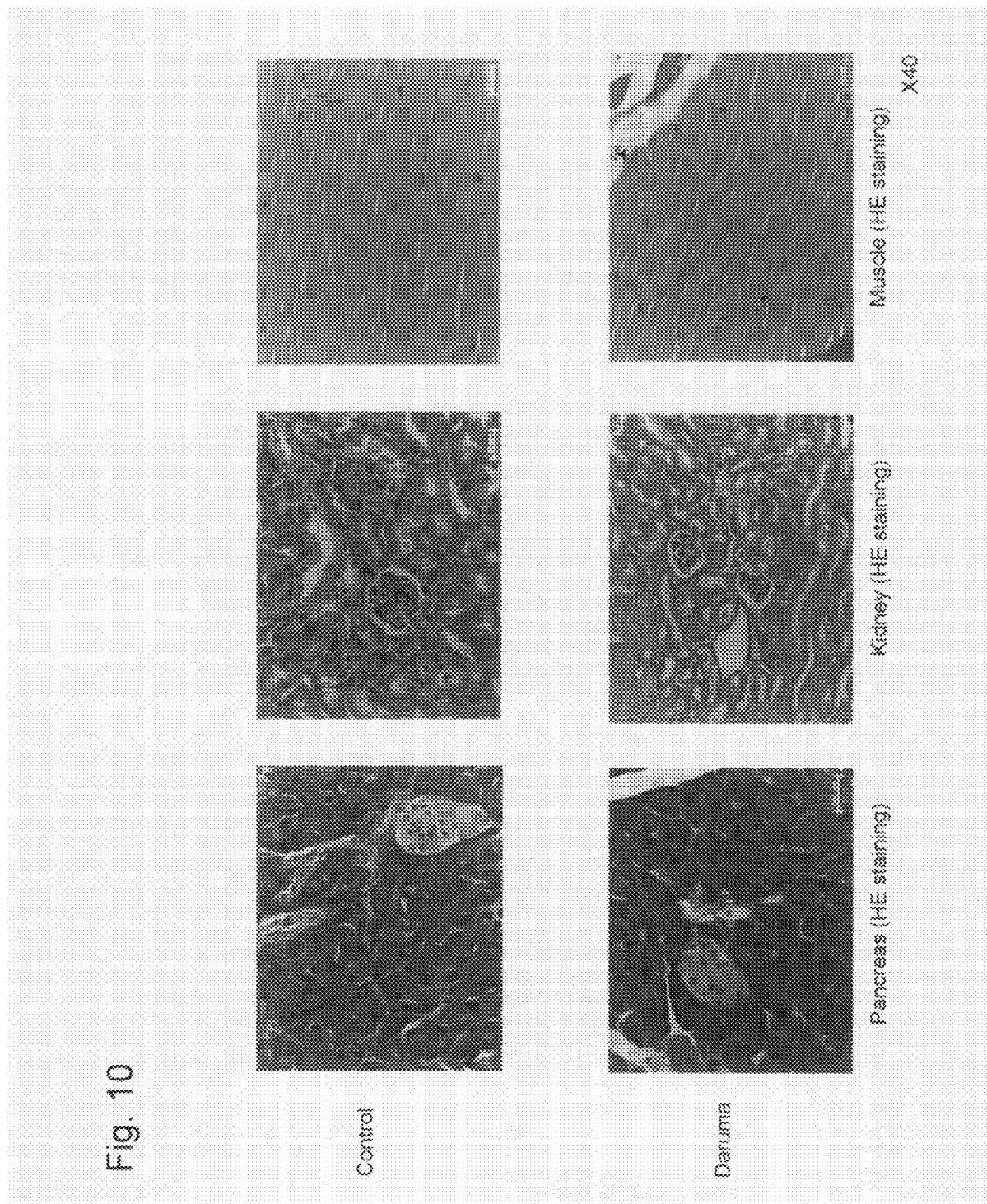
FIG. 10 is a set of photographs showing HE staining images of pancreas, kidney and muscle tissue sections between an obese Daruma mouse and a conventional mouse.

The pancreas, kidney and muscle were removed from obese Daruma and conventional mice to prepare tissue sections thereof, which were then subjected to HE staining for microscopic observation. FIG. 10 shows HE staining images thereof. No abnormalities were observed in the obese Daruma and conventional mice.

Example 3

Comparison with Other Obese Mice (Comparison of the Body Weight Gains and a Crossing Experiment)

When growth curves were prepared, it was found that the male and female Daruma mice started to show obesity from about 4 to 5 weeks of age after weaning and had a body weight of 1.5 times that of the control mice at 15 weeks of age and of about 2 times thereof at 20 weeks of age. When the time at which the Daruma mice started to show obesity was compared with that at which other model mice did, the time was late (about 6 to 8 weeks of age) in fat (fat) mice and (9 to 12 weeks of age) in tubby (tub) mice; obeseb (ob) and diabetes (db) mice started to become obese at an early stage of about 4 to 5 weeks of age. Thus, the obesity onset time in the Daruma mice was similar to those in the obese (ob) and diabetes (db) mice. Comparison of only the body weight increase rates showed that the body weight increase profile of the Daruma mice was similar to, rather than those of the obese (ob), diabetes (db) and tubby (tub) mice whose body weights gradually increased and reached plateaus at 50 to 60 g, that of the fat (fat) mice whose body weight rapidly increased compared to those of the three strains of mutated mice and finally reached 60 to 70 g.

In addition, for comparison with existing model mice at a gene level, heterozygous Daruma mice were crossed with various strains of model heterozygous mice. If the model mice have the same gene mutation as the Daruma mice, 25% of the children thereof should develop obesity because the cross is theoretically heterozygous. As a result, crossing with most of the strains of model mice provided children having an incidence rate of obesity of 0%. However, only the children born of crossing with diabetes (db) mice showed an incidence rate of obesity of 14%. From the results, it is probable that the obesity of the Daruma mice is at least not due to the mutation of the same gene as those of the obese (ob), fat (fat) and tubby (tub) mice. On the other hand, there is suggested the possibility that factors responsible for the obesity of the Daruma mice are common to those for the diabetes (db) mice because the crossing with the diabetes (db) mice resulted in the incident rate of obesity of 14%. However, if the gene responsible for the obesity of the Daruma mice is the same as that for the diabetes (db) mice, the children thereof are estimated to develop obesity with a probability of 25%; thus, it can be said to be certain that the responsible gene for the Daruma mice is different from that for the diabetes (db) mice (FIG. 11). Accordingly, it becomes possible to envisage the presence of an obesity risk factor common to both of the Daruma and db mice in addition to a direct risk factor for obesity An obesity gene unique to the Daruma mice is called Aa (a is a recessive gene; only aa leads to the development of obesity), and an obesity gene unique to the db mice, Cc (c is a recessive gene; only cc leads to the development of obesity). These genes are unique to only the respective strains of mice; thus, the db mice have AA for the A gene, and the Daruma mice have CC for the C gene. Accordingly, crossing between these strains of mice makes zero the probability that mice having aa or cc are born, resulting in no children thereof developing obesity. However, another factor causing obesity (which probably might as well be a risk factor) will be present; a gene therefor is called B. Assuming that this factor is not involved in the development of obesity in the intrastrain cross, but forms bb in the interstrain cross and induces obesity only in individuals having a and c, the probability of the induction of obesity is 13.8%. This value is close to 14%, the value achieved in the interstrain cross, which provides a convincing explanation for why the obesity was observed in the children born of the present interstrain crossing.

The obesity mouse strain Daruma of the present invention can be used not only as a model for basic research of obesity, feeding, energy metabolism or diabetes but also as a model for drug discovery or evaluation of health foods.

What is claimed is:

1. A mouse strain, Daruma, derived from ICR mice, which is obtained by crossing between mice obtained from a fertilized ovum having an accession number of FERM ABP-10888 and which spontaneously develop monogenic visceral fat type obesity, exhibiting autosomal recessive inheritance for the trait of spontaneously developing the visceral fat type obesity.

2. The mouse strain Daruma according to claim 1, further having concurrent diabetes and hyperlipemia.

3. The mouse strain Daruma according to claim 1, wherein the visceral fat type obesity is developed at four weeks of age.

4. The mouse strain Daruma according to claim 1, wherein the mouse strain is capable of being used as a model for human obesity and/or diabetes.

5. A method for evaluating, or screening for, health foods for preventing obesity or agents for treating obesity or diabetes, comprising administrating a test substance to mice of the strain Daruma according to claim 1 and determining the effect of the test substance on development of obesity or diabetes in the mice.

* * * * *